US009022948B2

(12) United States Patent
Wang

(10) Patent No.: US 9,022,948 B2
(45) Date of Patent: *May 5, 2015

(54) SYSTEM AND METHOD FOR LOCATING AND IDENTIFYING THE FUNCTIONAL NERVES INNERVATING THE WALL OF ARTERIES

(75) Inventor: Jie Wang, Englewood Cliffs, NJ (US)

(73) Assignee: Symap Holding Limited, Road Town, Tortola (VG)

(*) Notice: Subject to any disclaimer, the term of this patent is extended or adjusted under 35 U.S.C. 154(b) by 0 days.

This patent is subject to a terminal disclaimer.

(21) Appl. No.: 14/241,058

(22) PCT Filed: Aug. 24, 2012

(86) PCT No.: PCT/IB2012/054303
§ 371 (c)(1),
(2), (4) Date: Feb. 25, 2014

(87) PCT Pub. No.: WO2013/030738
PCT Pub. Date: Mar. 7, 2013

(65) Prior Publication Data
US 2014/0194866 A1 Jul. 10, 2014

Related U.S. Application Data

(60) Provisional application No. 61/527,893, filed on Aug. 26, 2011, provisional application No. 61/609,565, filed on Mar. 12, 2012.

(51) Int. Cl.
A61B 5/05 (2006.01)
A61B 18/14 (2006.01)
(Continued)

(52) U.S. Cl.
CPC ........... A61B 5/04001 (2013.01); A61B 5/0205 (2013.01); A61B 5/201 (2013.01);
(Continued)

(58) Field of Classification Search
CPC ....................................... A61B 5/4893
USPC ........ 600/546, 547, 554; 607/2, 40, 115, 116, 607/44; 606/32, 41
See application file for complete search history.

(56) References Cited

U.S. PATENT DOCUMENTS 5,836,875 A 11/1998 Webster, Jr. et al.
6,292,695 B1 9/2001 Webster, Jr. et al.
(Continued)

FOREIGN PATENT DOCUMENTS

AU 2011253826 6/2012
CN 201469401 U 5/2010
(Continued)

OTHER PUBLICATIONS

Jun. 27, 2013 US Restriction Requirement, U.S. Appl No. 13/219,171.
(Continued)

Primary Examiner — Max Hindenburg
Assistant Examiner — Jonathan M Foreman
(74) Attorney, Agent, or Firm — Law Offices of Albert Wai-Kit Chan, PLLC

(57) ABSTRACT

System and method for locating and identifying nerves innervating the wall of arteries such as the renal artery are disclosed. The present invention identifies areas on vessel walls that are innervated with nerves; provides indication on whether a dose of energy is delivered accurately to a targeted nerve; and provides immediate post-procedural assessment of the effect of the energy delivered to the nerve. The method includes at least the steps to evaluate a change in physiological parameters after a dose of energy is delivered to an arterial wall; and to determine the type of nerve that the energy was directed to (none, sympathetic or parasympathetic) based on the results of the evaluation. The system includes at least a device for delivering a dose of energy to the wall of an artery; sensors for detecting physiological signals from a subject; and indicators to display the results obtained using the said method.

17 Claims, 13 Drawing Sheets

(51) Int. Cl.
    *A61B 5/04*         (2006.01)
    *A61B 5/0205*     (2006.01)
    *A61B 5/20*         (2006.01)
    *A61B 5/00*         (2006.01)
    *A61B 18/18*       (2006.01)
    *A61B 18/00*       (2006.01)

(52) U.S. Cl.
    CPC ............ *A61B 5/4833* (2013.01); *A61B 5/4893* (2013.01); *A61B 18/1492* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61B 5/4836* (2013.01); *A61B 18/18* (2013.01)

(56) References Cited

U.S. PATENT DOCUMENTS

| | | | |
|---|---|---|---|
| 7,653,438 | B2 | 1/2010 | Deem et al. |
| 7,937,143 | B2 | 5/2011 | Demarais et al. |
| 2002/0120304 | A1 | 8/2002 | Mest |
| 2003/0216792 | A1 | 11/2003 | Levin et al. |
| 2007/0027496 | A1 | 2/2007 | Parnis et al. |
| 2007/0173899 | A1 | 7/2007 | Levin et al. |
| 2007/0265687 | A1 | 11/2007 | Deem et al. |
| 2010/0076519 | A1 | 3/2010 | Kornet et al. |
| 2010/0114244 | A1* | 5/2010 | Manda et al. ............... 607/60 |
| 2011/0092880 | A1 | 4/2011 | Gertner |
| 2011/0137298 | A1 | 6/2011 | Nguyen et al. |
| 2011/0184337 | A1 | 7/2011 | Evans et al. |
| 2011/0200171 | A1 | 8/2011 | Beetel et al. |
| 2011/0306851 | A1 | 12/2011 | Wang |
| 2011/0307034 | A1 | 12/2011 | Hastings et al. |
| 2012/0296329 | A1 | 11/2012 | Ng |

FOREIGN PATENT DOCUMENTS

| | | |
|---|---|---|
| CN | 102125460 A | 7/2011 |
| CN | 102551874 A | 7/2012 |
| CN | 102551878 A | 7/2012 |
| EP | 2460486 A1 | 6/2012 |
| WO | 2006041881 | 4/2006 |
| WO | 2006041881 A2 | 4/2006 |
| WO | 2007103879 A2 | 9/2007 |
| WO | 2008003058 A2 | 1/2008 |
| WO | 2008061150 A2 | 5/2008 |
| WO | 2012068471 | 5/2012 |

OTHER PUBLICATIONS

Aug. 28, 2013 US Office Action, U.S. Appl. No. 13/219,171.
Feb. 5, 2014 Notice of Allowance and Fees Due, U.S. Appl. No. 13/219,171.
Feb. 14, 2014 Notice of Acceptance, AU 2012303701.
Shah et al., 2012, "Irrigated Radiofrequency Ablation Catheter and Electro-Anatomical Mapping with Computerized Tomography integration for Renal Artery Sympathetic Denervation" J. Inasive Cardiology 24 (12): E208-E310.
Schlaich et al., 2009, "Renal Denervation as a Therapeutic Approach for Hypertension: Novel Implications for an Old Concept" Hypertension, 55, 1195-1201.
Takenaka et al., 2007, "Pelvic Autonomic Nerve Mapping Around the Prostate by Intraoperative Electrical Stimulation with Simultaneous Measurement of Intracavernous and Intraurethral Pressure" J. of Urology vol. 177, pp. 225-229.
Mar. 20, 2014 Second Examiner's Report, AU 2012303696.
May 14, 2014 Notice of Acceptance, AU 2012303701.
May 7, 2014 First Office Action, CN 201310070218.X.
Apr. 28, 2014 Search report, CN 201310070218.X.
Messerli et al., 2014, "Renal Denervation for Resistant Hypertension?", The New England Journal of Medicine.
Jan. 10, 2013 PCT International Search Report, Int'l App'l No. PCT/IB2012/054303.
Jan. 10, 2013 PCT International Search Report, Int'l App'l No. PCT/IB2012/054310.
Jan. 10, 2013 PCT Written Opinion, Int'l App'l No. PCT/IB2012/054303.
Jan. 10, 2013 PCT Written Opinion, Int'l App'l No. PCT/IB2012/054310.
May 10, 2013 First Examiner's Report, AU 2012303696.
May 16, 2013 First Examiner's Report, AU 2012303701.
Aars, H. and Akre, S., (1970), Reflex Changes in Sympathetic Activity and Arterial Blood Pressure Evoked by Afferent Stimulation of the Renal Nerve, Acta Physiol. Scand., 78 (2): 184-188.
Beacham, W.S. and Kunze, D.L., (1969), Renal Receptors Evoking a Spinal Vasometer Reflex, J. Physiol., 201 (1): 73-85.
Brinkmann et al., (2012), Catheter-Based Renal Nerve Ablation and Centrally Generated Sympathetic Activity in Difficult-to-Control Hypertensive Patients: Prospective Case Series, Hypertension, 60: 1485-1490.
Campese et al., 1995, "Renal afferent denervation prevents hypertension in rats with chronic renal failure", Hypertension, 25(4 Pt. 2): 878-882.
Campese et al., 2002, "Neurogenic factors in renal hypertension", Current Hypertension Reports, 4(3):256-260.
Chinushi et al., 2013, Blood Pressure and Autonomic Responses to Eletrical Stimulation of the Renal Arterial Nerves Before and After Ablation of the Renal Artery, Hypertension, 61: 450-456.
Converse, R.L. Jr.et al., 1992, "Sympathetic overactivity in patients with chronic renal failure", New England Journal of Medicine, 327(27):1912-1918.
Dibona et al., 1997, "Neural Control of Renal Function", Physiological Reviews, 77(1): 75-197.
DiBona, G.F., 2003, "Neural control of the kidney: past, present and future", Hypertension, 41: 621-624.
Esler, M. et al, 1990, "Overflow of catecholamine neurotransmitters to the circulation: source, fate, and functions", Physiological Reviews, 70(4):963-985.
Esler, M. et al., 2009, "Catheter-based renal denervation reduces total body and renal noradrenaline spillover and blood pressure in resistant hypertension", Journal of Hypertension, 27(suppl 4):s167. Presented at the 2009 European Meeting on Hypertension.
Esler, M. et al., 2010, "Renal sympathetic denervation in patients with treatment-resistant hypertension (The Symplicity HTN-2 Trial): a randomized controlled study", The Lancet, 376: 1903-1909.
Krum, H. et al., 2009, "Catheter-based renal sympathetic denervation for resistant hypertension: a multicentre safety and proof-of-principle cohort study", The Lancet, 373(9671):1275-1281.
Lv, M., Wei, S.G. and Chai, X.S., (1995), Effect of Electrical Stimulation of Afferent Renal 30 Nerve on Arterial Blood Pressure, Heart Rate and Vasopressin in Rabbits, Acta Physiol. Sinica, 47 (5): 471-477.
Ma, G. and Ho, S.Y., (1990), Hemodynamic Effects of Renal Interoreceptor and Afferent Nerve Stimulation in Rabbit, Acta Physiol. Sinica, 42 (3): 262-268.
Mahfoud, F. et al., 2011, "Effect of Renal Sympathetic Denervation on Glucose Metabolism in Patients With Resistant Hypertension: A Pilot Study", Circulation 123(18): 1940-1946.
Medical devices: p. 1-2, Feb. 22, 2012.
Persu et al., 2013 Editorial Commentary on "Electric Nerve Stimulation to Monitor the Efficacy of Renal Denervation" Jan. 4, 2013, Hypertension.
Schlaich, M.P. et al, 2009, "Renal Sympathetic-Nerve Ablation for Uncontrolled Hypertension", New England Journal of Medicine, 361(9): 932-934.
Schlaich, M.P. et al., 2009, "A novel catheter based approach to denervate the human kidney reduces blood pressure and muscle sympathetic nerve activity in a patient with end stage renal disease and hypertension.", Journal of Hypertension, 27(suppl 4):s154. Presented at the 2009 European Meeting on Hypertension.
Smithwick, R.H. et al., 1953, "Splanchnicectomy for essential hypertension; results in 1,266 cases.". J Am Med Association, 152(16):1501-1504.

(56) References Cited

OTHER PUBLICATIONS

Talenfeld, A.D. et al., 2007, "MDCT Angiography of the Renal Arteries in Patients with Atherosclerotic Renal Artery Stenosis: Implications for Renal Artery Stenting with Distal Projection", American Journal of Roentgenology, 188: 1652-1658.

Ueda, H., Uchida, Y., and Kamisaka, K., (1967), Mechanism of the Reflex Depressor Effect by Kidney in Dog, Jpn. Heart J., 8 (6): 597-606.

Valente, J.F. et al., 2001, "Laparoscopic renal denervation for intractable ADPKD-related pain." Nephrology Dialysis Transplantation, 16(1): 160.

Vigilance D.W. et al., (2005), "A novel approach to increase total urine output in acute heart failure: unilateral renal nerve blockade." Journal of the American College of Cardiology Supplement 2005, 45(3):166A.

Ye, S. et al., 2002, "Renal injury caused by intrarenal injection of phenol increases afferent and efferent sympathetic nerve activity", American Journal of Hypertension, 15(8): 717-724.

Michael Weistein, 2011, "Renal Denervation: The next big thing in cardiovascular devices", North America Equity Research, J.P.Morgan.

Levin, Nov. 2009, "Ardian: Succeeding where drugs fail—treating hypertension in the cath lab", In vivo: the business & medicine report, 22-29.

Chan et al. 2007, "Ultrasound guidance improves success rate of axillary brachial plexus block", Can J Anesth, 54: 3, pp. 176-182.

Jose et al., 2007, Correspondence to the editor on "Ultrasound guidance improves success rate of axillary brachial plexus block", Can J Anesth 54: 7.

Mannion et al., 2007, Correspondence to the editor on "Ultrasound guidance improves success rate of axillary brachial plexus block", Can J Anesth 54: 7.

Sia et al., 2005, "A Comparison of Proximal and Distal Radial Nerve Motor Responses in Axillary Block Using Triple Stimulation", Regional Anesthesia and Pain Medicine, 30: 5, pp. 458-463.

Tsui, 2007, "Ultrasound-guidance and nerve stimulation: implications for the future practice of regional anesthesia", Can J Anesth, 54: 3, pp. 165-170.

Oct. 7, 2014 Office Action for U.S. Appl. No. 14/241,061.

\* cited by examiner

X > a   => sympathetic nerve
X < -b  => parasympathetic nerve
X ≈ 0   => no functioning nerves where values of a and b were
determined empirically from a large
statistical group

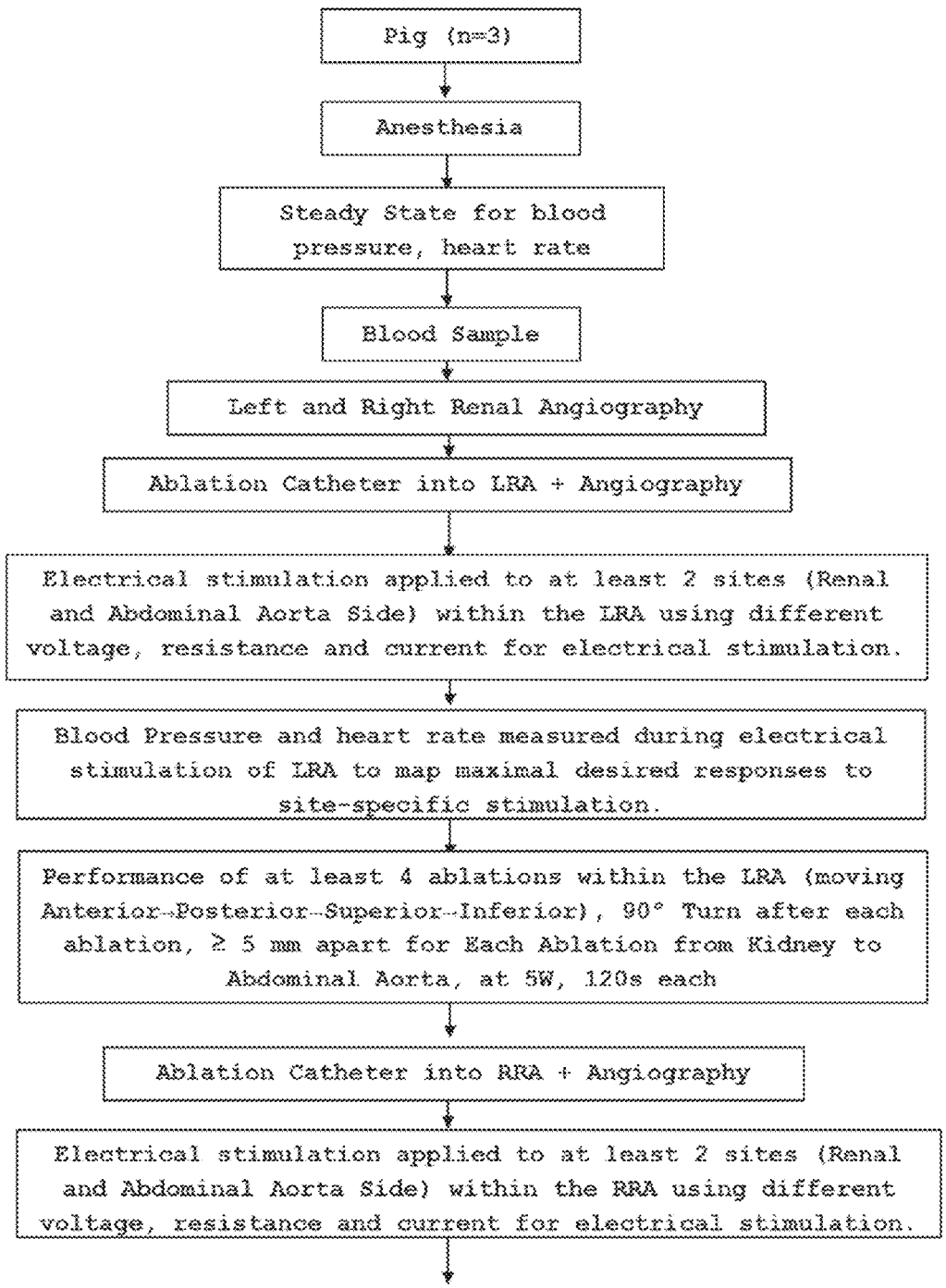

4A

4B

Figures 4C-D
4C
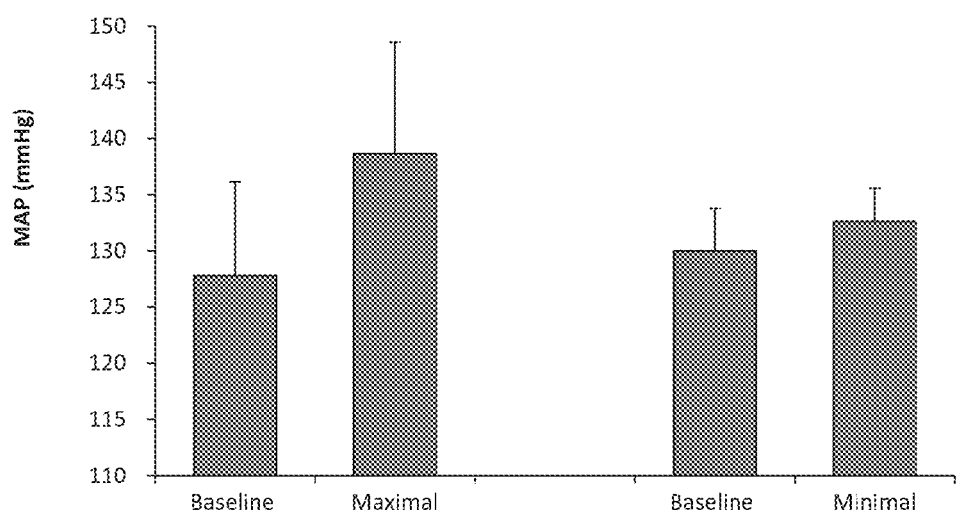
4D
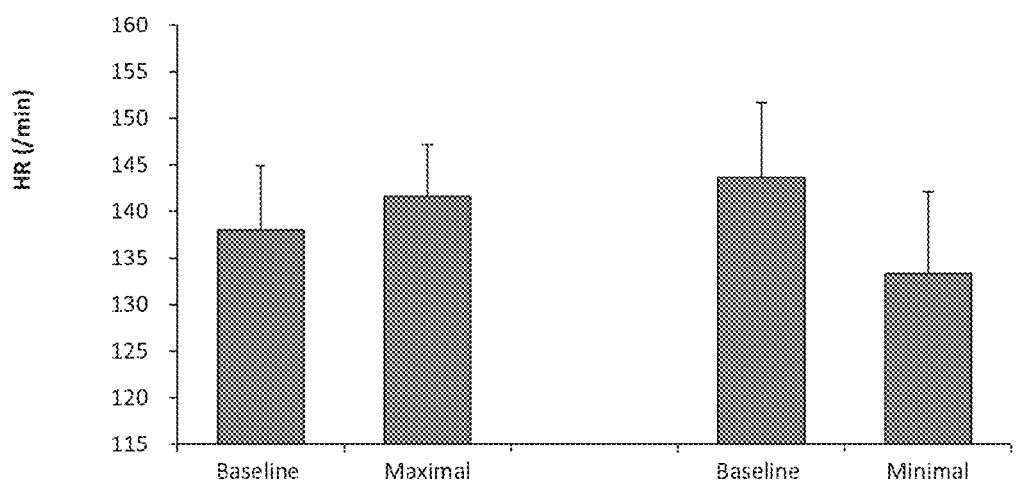

5A

5B

5C

5D

7A

7B

7C

7D

8A

8B

8C

8D

SYSTEM AND METHOD FOR LOCATING AND IDENTIFYING THE FUNCTIONAL NERVES INNERVATING THE WALL OF ARTERIES

CROSS-REFERENCE TO RELATED APPLICATIONS

This application is the National Stage of International Application No. PCT/IB2012/054303, filed Aug. 24, 2012, which claims priority of U.S. Ser. No. 61/609,565, filed Mar. 12, 2012 and U.S. Ser. No. 61/527,893, filed Aug. 26, 2011. The contents of the preceding applications are hereby incorporated in their entireties by reference into this application. Throughout this application, various publications are referenced. Disclosures of these publications in their entireties are hereby incorporated by reference into this application in order to more fully describe the state of the art to which this invention pertains.

FIELD OF THE INVENTION

This invention relates to a system and method for accurate and precise location and identification of areas innervated with sympathetic and parasympathetic related nerves on an arterial wall during and after an energy delivery process.

BACKGROUND OF THE INVENTION

The fact that some cases of hypertension are resistant to treatment by pure pharmacological means has reignited the use of invasive techniques in treating these cases. Historically, surgical renal denervation was the prominent treatment for severe cases of hypertension prior to the introduction of orally administered anti-hypertensive drugs (Smithwick and Thompson, 1953). This type of conventional surgery was, however, extremely invasive and involved a major surgical procedure which greatly limits it practicality (DiBona, 2003). At least two clinical studies have, to a certain extent, provided support to the use of minimally invasive catheter-based radiofrequency (RF) renal nerve ablation in the treatment of resistant hypertension (Krum et al., 2009; Esler et al., 2009). Patients with hypertension resistant to the available anti-hypertensive drugs were selected for these studies and this interventional procedure demonstrated a 89% clinical success rate in lowering their blood pressure in a small and very selective patient population.

While there is growing interest in using such minimal invasive interventional techniques for treatment of hypertension, all systems on the market, including the Ardian Symplicity® Catheter System, are not optimally designed for this purpose. There are apparent shortcomings, even in the Ardian Symplicity® Catheter System, that limit the certainty of the interventional outcome.

An important aspect not considered in the current interventional systems and techniques, is the precision and accuracy in locating and delivering an effective dose of energy to a suitable ablation spot in the arterial wall. The current commonly accepted procedures for performing renal nerve ablation via catheters typically consists the steps of administering to the arterial wall 4 to 6 ablations, each made by 2 minutes of RF energies and spaced both longitudinally and rotationally along the inner wall of each renal artery. The ablations had to be delivered "blindly" in this helical manner because the exact location of the nerves innervating the renal artery with respect to the ablation catheter is unknown before and during the delivery of the ablation energy. An inaccurately directed dose of energy not only causes unnecessary damage to healthy tissues and non-sympathetic nerves but more importantly could not provide the promised solution for hypertension which the interventional procedure was intended for. In fact, in certain clinical settings other than the two published studies, the responder rate of the current "blind" type of interventional procedure could go as low as 50% (Medical devices: pg 1-2, Feb. 22, 2012).

Theoretically, precise nerve ablation in the wall of an artery could be achieved by mapping the location of the nerves innervating the arterial wall prior to delivery of the dose of energy. By monitoring physiological parameters associated with the autonomic nervous systems such as the blood pressure, heart rate and muscle activity while a stimulus is delivered to a selected location on the arterial wall, the presence of autonomic nerves in the immediate vicinity of this location will be reflected from the changes in the monitored physiological parameters (Wang, US 2011/0306851 A1).

Further, the sympathetic and parasympathetic nerves of the autonomic nervous system often exert opposite effects in the human body including their control on blood pressure and heart rate. While ablation of the sympathetic nerves innervating the arterial walls will relieve hypertension, there is an equally possible chance that other tissues such as parasympathetic nerves are ablated in the "blind" type of interventional procedure. The result for decreasing or removal of nerve activity blindly may worsen the hypertension as could be inferred from several animal studies (Ueda et al., 1967; Beacham and Kunze, 1969; Aars and Akre, 1970; Ma and Ho, 1990; Lu et al. 1995).

The cause of failure in the current treatment was attributed to regeneration of the nerves after the ablation (Esler et al., 2010) and may also be related to both the inability to deliver the dose of energy to the targeted nerve and an insufficient dose of energy delivered for effective ablation. At present, the success of renal denervation is only assessed by the measurement of a secondary effect known as norepinephrine spillover at least days after the interventional procedure (Krum et al., 2009) and lack a method for immediate post-procedural assessment. In order to improve the success rate of the interventional procedure, it is important to not only locate suitable ablation spots on the arterial wall, but also ensure that the energy is precisely and accurately delivered to a targeted nerve during the ablation process, and confirm immediately after the ablation that the dosage of energy delivered has effectively ablated the targeted nerve.

In response to the shortcomings of the current system and methods for nerve ablation, the present invention introduces improvements by providing a system and methods for accurate and precise location of suitable ablation spots on a renal arterial wall; ensuring sufficient ablation energy is accurately directed into a targeted nerve and to conduct immediate post-procedural assessment of nerve ablation.

SUMMARY OF THE INVENTION

It was with the preceding needs in mind that the present invention was developed. Embodiments of the disclosure are directed to system and method for accurate and precise location of areas innervated with nerves on an arterial wall; ensuring sufficient energy is accurately directed into a targeted nerve to elicit a desired response such as stimulation and ablation; and to conduct immediate post-procedural assessment of a sufficient nerve ablation. Further, the embodiments of the disclosure are also directed to provide an interface for clear representation of the location and type of nerves that are innervating the location being probed on the arterial wall.

The present invention provides a method for identifying the presence of functional sympathetic and parasympathetic nerves innervating the arterial walls in a human body with respect to the location of a dose of energy. The method comprises one or more of the steps of preparing a baseline of one or more of physiological parameters prior to the delivery of a dose of energy to the arterial wall; delivering a dose of energy to the arterial wall; detecting the physiological changes as a result of the delivered energy; rating the change based on a set of empirically pre-determined values; and determining if the area where the energy was delivered lies in the vicinity of functioning sympathetic or parasympathetic nerves based on the ratings.

In one embodiment, said method is used for locating suitable nerve ablation sites relevant to baroreflex including both sympathetic and parasympathetic systems in arterial walls prior to a nerve ablation procedure. In certain embodiments, the nerve ablation procedure is for denervation of the renal artery. In another embodiment, the method is used for ensuring the accurate delivery of ablation energy to a targeted nerve in the arterial wall during a nerve ablation process. In a further embodiment, the method is used for immediate post-procedural assessment of the nerve ablation process to ensure that the targeted nerve has been ablated by the energy delivered in a nerve ablation procedure.

In certain embodiments, the energy is delivered to the arterial wall at dosage suitable for nerve stimulation. In other embodiments, the energy is delivered to the arterial wall at a dosage suitable for nerve ablation.

In one embodiment, the physiological parameters comprise blood pressure, heart rate, levels of biochemicals selected from epinephrine, norepinephrine, renin-angiotensin II and vasopressin, cardiac electrical activity, muscle activity, skeletal nerve activity, action potential of cells or other measurable reactions as a result of these physiological changes such as pupil response, electromyogram and vascular constriction.

In some embodiments, an area on the arterial wall that, upon stimulation, causes increase in blood pressure and heart rate is considered as innervated with sympathetic nerves while, in contrary, an area on the arterial wall that, upon stimulation, causes decrease in blood pressure and heart rate is considered as innervated with parasympathetic nerves.

In an embodiment, the energy for ablation is considered to be delivered accurately to a targeted nerve innervating the arterial wall when the physiological parameters deviate significantly from the baseline during the ablation process.

In one embodiment, the nerve ablation procedure is considered to be successful when an area, confirmed to be innervated with nerves with said method before the delivery of ablation energy, no longer leads to changes in the physiological parameters such as blood pressure and heart rate when stimulation energy is delivered to this spot.

The present invention also provides a system for locating and identifying nerves innervating an arterial wall. The system comprises one or more devices capable of delivering a dose of energy to an arterial wall; one or more sensors to receive signals of physiological parameters; one or more devices for analysis of signals from the sensors; and one or more indicators or panels capable of displaying the results of the analysis.

In one embodiment, the dose of energy delivered by the energy delivery device can be controlled to achieve either nerve stimulation or nerve ablation. In another embodiment, two separate devices are used to carry out nerve stimulation and nerve ablation independently.

In another embodiment, the energy delivered is one or more of electrical, mechanical, ultrasonic, radiation, optical and thermal energies.

In some embodiments, said sensors detect physiological parameters which comprise blood pressure, heart rate, levels of biochemicals selected from epinephrine, norepinephrine, renin-angiotensin II and vasopressin, cardiac electrical activity, muscle activity, skeletal nerve activity, action potential of cells and other measurable reactions as a result of the above such as pupil response, electromyogram and vascular constriction. In certain embodiments, the signals corresponding to the physiological parameters are detected with commercially available technologies known in the field.

In another embodiment, the device for digital analysis of the physiological signals is a microcontroller or computer.

In one embodiment, the analyzed results are displayed using different colored indicators. An area innervated with sympathetic nerves is represented with a green indicator and an area innervated with parasympathetic nerves is represented with a red indicator. In another embodiment, the analyzed data are displayed on a digital viewing panel.

In one embodiment, the set of indicators or panels may be built into devices in the system such as the energy delivery device. In certain embodiments, the set of indicators or panels may exist as a separate entity in the system.

BRIEF DESCRIPTION OF THE FIGURES

FIG. 4C shows Maximal and Minimal Effects of Left Renal Artery Stimulation on Mean Arterial Pressure (MAP). Shown is mean arterial pressure (MAP, as measured in mmHG) after an electrical stimulation in the left renal artery (LRA); baseline measures, as well as maximal and minimal responses after the stimulation are shown.

FIG. 4D shows Maximal and Minimal Effects of Left Renal Artery Stimulation on Heart Rate (HR). Shown are maximal and minimal changes in heart rate after left renal artery (LRA) electrical stimulation; baseline measures, as well as maximal and minimal heart rates after the stimulation are shown.

DETAILED DESCRIPTION OF THE INVENTION

This invention provides a system and method for locating sites innervated with functional nerves in the wall of arteries, particularly the renal artery, though persons skilled in the art will appreciate that nerves innervating other arteries or vessels in the human body may be located using this invention. The system comprises one or more devices capable of delivering a dose of energy to the wall of an artery; one or more sensors to receive inputs of physiological signals; one or more devices for analysis of signals from the sensors; and one or more indicators or panels capable of displaying the results of the analysis.

Figure 1:
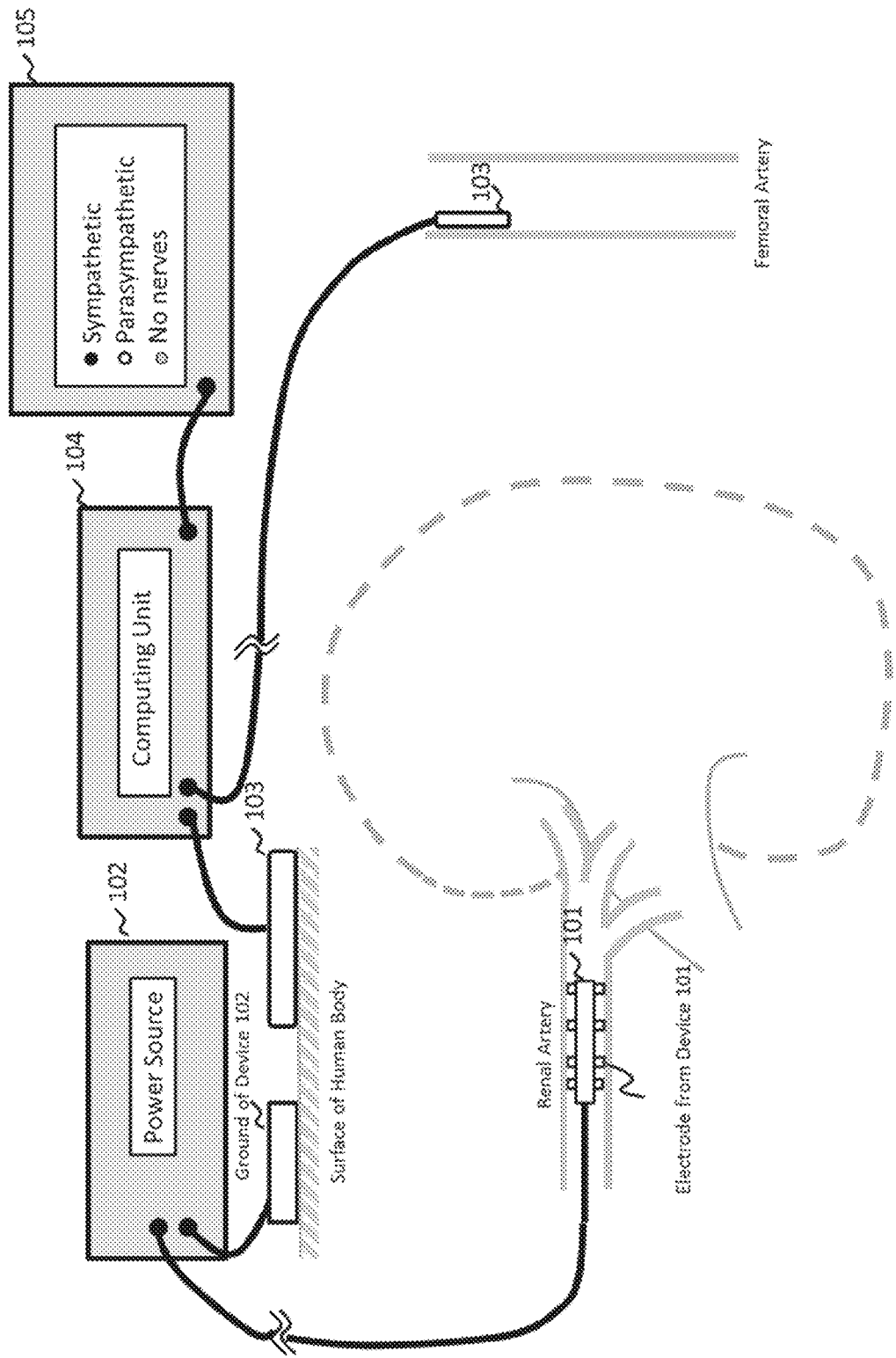
FIG. 1 is a schematic of a system of the present invention for locating and identifying functional nerves innervating the wall of an artery. The system comprises device 1 for delivery of energy to the arterial wall; power source 2 for powering device 1; sensor 3 for detecting signals of physiological parameters; device 4 for analyzing the data from sensor 3; and indicator 5 to display the results from device 4.

FIG. 1 depicts an exemplary system in accordance with an aspect of the invention, namely a renal denervation system using blood pressure and heart rate as the physiological parameters for identifying nerve response. The system comprises one or more of devices 1 for delivery of energy to the arterial wall which is in electrical communication with a power source 2. System further comprises sensors 3 for detecting physiological signals in electrical communication with device 4 for analysis of the physiological signals. The indicator 5 in electrical communication with device 4 displays the result of the analysis from device 4. Device 1, in the form of a dual-function catheter, is shown inserted into the renal artery via minimal invasive interventional procedure in this embodiment. At least one of the electrodes of device 1 contacts the renal arterial wall at a defined location and is capable of delivering a dose of energy from the power source 2 for stimulation or ablation of the nerves that may be innervating the area of the arterial wall for which the electrode is in contact with. Sensors 3 detect changes in blood pressure and/or heart rate as energy sufficient for nerve stimulation or ablation is delivered from an electrode on device 1 to the spot the electrode is contacting on the arterial wall. The signals from sensor 3 will be inputted to device 4 which will determine digitally whether the signal elicited is due to sympathetic or parasympathetic nerves, or the lack thereof. Indicator 5 will then display the result of the analysis from device 4.

In one embodiment of the invention, device 1 is an invasive device inserted into an artery capable of delivering energy to a nerve innervating the artery, resulting in nerve stimulation or ablation. In another embodiment, device 1 is made up of two separate entities, one delivering the energy for nerve stimulation, and the other nerve ablation. In a different embodiment, device 1 is a single-electrode catheter or multi-electrode catheter.

In one embodiment, power source 2 delivers energy to the arterial wall via device 1. In another embodiment, energy is delivered remotely through the human body by power source 2 into the arterial wall without device 1. In a further embodiment, power source 2 is a multi-channel power source capable of delivering separate doses of energy independently to distinct locations on the arterial wall. In other embodiments, power source 2 is a single channel power source capable of delivering only 1 dose of energy each time. In another embodiment, the dosage of energy to be delivered by power source 2 is adjustable to induce different effects on a targeted nerve such as stimulation or ablation. In further embodiments, the energy delivered by power source 2 is one or more of electrical, mechanical, ultrasonic, radiation, optical and thermal energies.

In one embodiment, sensors 3 detect signals from physiological parameters comprising blood pressure, heart rate, levels of biochemicals selected from epinephrine, norepinephrine, renin-angiotensin II and vasopressin, cardiac electrical activity, muscle activity, skeletal nerve activity, action potential of cells and other measurable reactions as a result of the above such as pupil response, electromyogram and vascular constriction. In a further embodiment, sensors 3 detect said signals externally with or without contacting any part of the human body. In another embodiment, sensors 3 detect said signals inside the human body by placing into contact with, or in the vicinity of, the lumen of interest such as the renal artery or femoral artery or any other artery. In yet another embodiment, sensor 3 could be a sensor from part of another equipment that is used in conjunction with this invention during the interventional procedure.

In an embodiment, device 4 is one or more microcontrollers or computers capable of digital analysis of the signals arising directly or indirectly from sensor 3.

In one embodiment, indicator 5 is one or more digital viewing panels that display the result from the analysis of device 4. In another embodiment, one or more results of said analysis from multiple locations on the arterial wall are simultaneously displayed on indicator 5. In a further embodiment, indicator 5 also displays one or more the physiological signals from sensor 3; energy related information from power source 2 such as current, frequency, voltage; tissue-electrode interface related information such as impedance; and information related to device 1 such as temperature. In certain embodiments, indicator 5 comprises a set of different colored lights each distinctly representing sympathetic nerve, parasympathetic nerve or no nerve. In other embodiments, indicator 5 represents the result from analysis of device 4 with texts, symbols, colors, sound or a combination of the above.

In certain embodiments, device 4 and indicator 5 are integrated as a single device and, in further embodiments, both device 4 and indicator 5 are integrated into power source 2.

In yet another embodiment, sensor 3, device 4 and indicator 5 exist independently from device 1 and power source 2 such that sensor 3, device 4 and indicator 5 can be used with other external or invasive methods for energy delivery into the vessel wall such as high-intensity focused ultrasound.

The present invention additionally provides a method for identifying the presence of functional sympathetic or parasympathetic nerves innervating a selected area on the arterial wall based on changes in physiological parameters induced by a dose of energy. The method comprises one or more of the steps of preparing a baseline of the physiological parameters to be measured prior to the delivery of a dose of energy to the arterial wall; delivering a dose of energy to the arterial wall; detecting the physiological changes as a result of the delivered energy; rating the change based on a set of empirically pre-determined values; and, based on the ratings, determining if there are functional sympathetic or parasympathetic nerves in the vicinity of the site of energy delivery.

Figure 2:
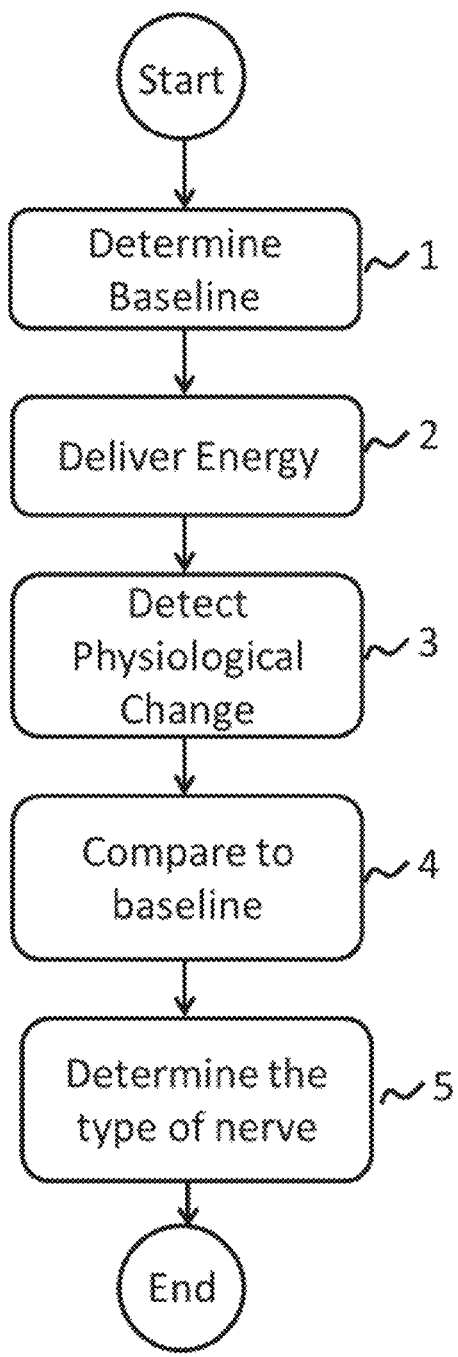
FIG. 2 is a schematic diagram depicting the steps in an embodiment of the method to determine whether functioning sympathetic or parasympathetic nerves are in the vicinity of a dose of energy delivered to the arterial wall. The graphs illustrate possible recorded physiological signals.
Figure 2:
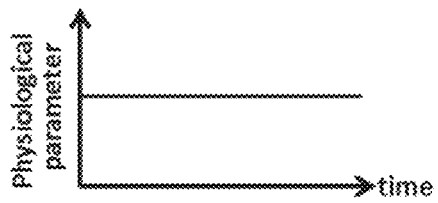
Figure 2:
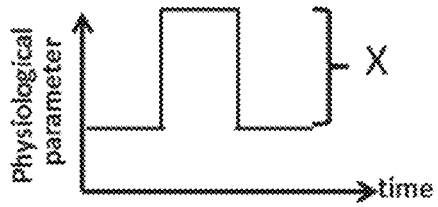

FIG. 2 is a flow chart illustrating the steps of the method for determining the presence of any functional sympathetic or parasympathetic nerve innervating a selected area of an arterial wall.

At step 1, physiological signals from sensor 3 are continuously recorded by device 4 to produce a reliable baseline reflective of any instantaneous changes in the signals.

Energy is then delivered by one of the electrodes in device 1 to the area on the arterial wall that this electrode is in contact with (Step 2). Sensor 3 detects any physiological change caused by the energy delivered, and the change is recorded as signals which are then sent to device 4. (Step 3)

In step 4, device 4 determines the deviation of the physiological signals from the baseline of step 1 and, in step 5, determines the type of nerves innervating the area on the arterial wall based on the deviation from the baseline information.

In one embodiment, the physiological signals detected by sensor 3 comprises one or more of blood pressure, heart rate, levels of biochemicals selected from epinephrine, norepinephrine, renin-angiotensin II and vasopressin, cardiac electrical activity, muscle activity, skeletal nerve activity, action potential of cells and other observable body reactions as a result of the above such as pupil response and vascular constriction.

In an embodiment, the dosage of energy delivered in step 2 is adjustable to induce different interactions with a targeted nerve such as nerve stimulation or nerve ablation.

In certain embodiments, the values of the physiological signals are measured using other external devices and inputted into device 4 prior to the energy delivery to replace the baseline formed by device 4.

In one embodiment, the changes in physiological parameters are detected during or after the energy delivery process in step 2. In another embodiment, the changes in physiological parameters are in the form of numerical values or waveforms. In further embodiments, the deviation from baseline of step 1 is evaluated by subtracting the baseline of step 1 from the signals.

In one embodiment, the empirically pre-determined set of values could be obtained from sets of clinical data or deduced from the experience of clinical physicians. In some embodiments, an area on the arterial wall is considered to be innervated with sympathetic nerves when energy delivered to the area causes an increase in heart rate by 10 beats per minute and/or an increase in blood pressure by 6 mmHg. In other embodiments, an area on the arterial wall is considered to be innervated with parasympathetic nerves when energy delivered to the area causes a decrease in heart rate by 5 beats per minute and/or a decrease in blood pressure by 2 mmHg.

In a further embodiment, the results of step 5 will be displayed on indicator 5.

In one embodiment, the method is used for identifying the suitable sites for nerve ablation in the arterial wall to disrupt baroreflex via sympathetic and parasympathetic nervous systems. In another embodiment, the method provides indication of whether the ablation energy is delivered accurately to the targeted nerves in the arterial wall. In a further embodiment, the method is used for immediate post-procedural assessment of nerve ablation.

The present invention also provides a method for locating or identifying a functional nerve innervating the wall of a blood vessel in a subject, comprising the steps of a) Delivering energy to one or more locations on said vessel wall sufficient to change one or more physiological parameters associated with the innervation of said vessel by a sympathetic or parasympathetic nerve; and b) Measuring said one or more physiological parameters after each delivery of energy, and determining the change from the corresponding parameters obtained without energy delivery to said vessel; wherein a lack of change in said physiological parameters in step b indicates the absence of a functional nerve at the location of energy delivery, a significant change in said physiological parameters in step b indicates the presence of a functional nerve at the location of energy delivery, and the direction of change in said physiological parameters in step b determines the nerve to be sympathetic or parasympathetic at the location of energy delivery. In one embodiment, the blood vessel is an artery, including a renal artery. In one embodiment, the functional nerve is related to baroreflex. In another embodiment, the subject of the method is a human or non-human animal. It is to be understood that a lack of change means that the change would be considered by someone skilled in the art to be negligible or statistically insignificant, and a significant change means that the change would be considered by someone skilled in the art to be meaningful or statistically significant.

In one embodiment, the method used for locating or identifying a functional nerve innervating the wall of a blood vessel in a subject comprises a step of delivering energy to a location where a nerve has been ablated, wherein a lack of change in said physiological parameters confirms nerve ablation. In one embodiment, the energy delivered is adjustable and consists of electrical, mechanical, ultrasonic, radiation, optical and thermal energies. In another embodiment, the energy delivered causes nerve stimulation or nerve ablation.

In one embodiment, the physiological parameters described in the method used for locating or identifying a functional nerve innervating the wall of a blood vessel in a subject are selected from blood pressure, heart rate, cardiac electrical activity, muscle activity, skeletal nerve activity, action potential of cells, pupil response, electromyogram, vascular constriction, and levels of biochemicals selected from epinephrine, norepinephrine, renin-angiotensin II and vasopressin. In another embodiment, the functional nerve is a sympathetic or parasympathetic nerve.

In one embodiment, a system for locating or identifying a functional nerve innervating the wall of a blood vessel in a subject comprises: a) an energy-delivering device configured to deliver energy to one or more locations on said wall sufficient to stimulate a nerve innervating said vessel; b) One or more measuring devices for measuring one or more physiological parameters associated with the innervation of said blood vessel by a sympathetic or parasympathetic nerve, before or after energy is delivered to said nerve by said energy-delivering device; and c) a device configured to couple to the one or more measuring devices for displaying the location and identity of a nerve innervating said vessel wall. In one embodiment, the measuring devices are placed inside the vessel or outside the body. In another embodiment, the measuring devices comprise one or more microcontrollers or computers.

In one embodiment, said system displays the location and identity of a nerve as numbers, texts, symbols, colors, sound, waveforms, or a combination thereof.

In one embodiment, said system is used in a method for locating or identifying a functional nerve innervating the wall of a blood vessel in a subject, comprising the steps of a) Delivering energy to one or more locations on said vessel wall sufficient to change one or more physiological parameters associated with the innervation of said vessel by a sympathetic or parasympathetic nerve; and b) Measuring said one or more physiological parameters after each delivery of energy, and determining the change from the corresponding parameters obtained without energy delivery to said vessel; wherein a lack of change in said physiological parameters in step b indicates the absence of a functional nerve at the location of energy delivery, a significant change in said physiological parameters in step b indicates the presence of a functional nerve at the location of energy delivery, and the direction of change in said physiological parameters in step b determines the nerve to be sympathetic or parasympathetic at the location of energy delivery.

It will be appreciated by persons skilled in the art that the system and method disclosed herein may be used in nerve ablation of the renal artery to disrupt baroreflex via sympathetic and parasympathetic nervous systems but its application could be extended to any innervated vessels in the body.

The invention will be better understood by reference to the Experimental Details which follow, but those skilled in the art will readily appreciate that the specific examples are for illustrative purposes only and should not limit the scope of the invention which is defined by the claims which follow thereafter.

It is to be noted that the transitional term "comprising", which is synonymous with "including", "containing" or "characterized by", is inclusive or open-ended and does not exclude additional, un-recited elements or method steps.

EXAMPLE 1

Locating Nerves Innervating an Arterial Wall

A method to locate nerves innervating an arterial wall via examination of the changes in physiological parameters after the delivery of a suitable dose of energy was designed and executed in acute pig experiments.

Figure 3:
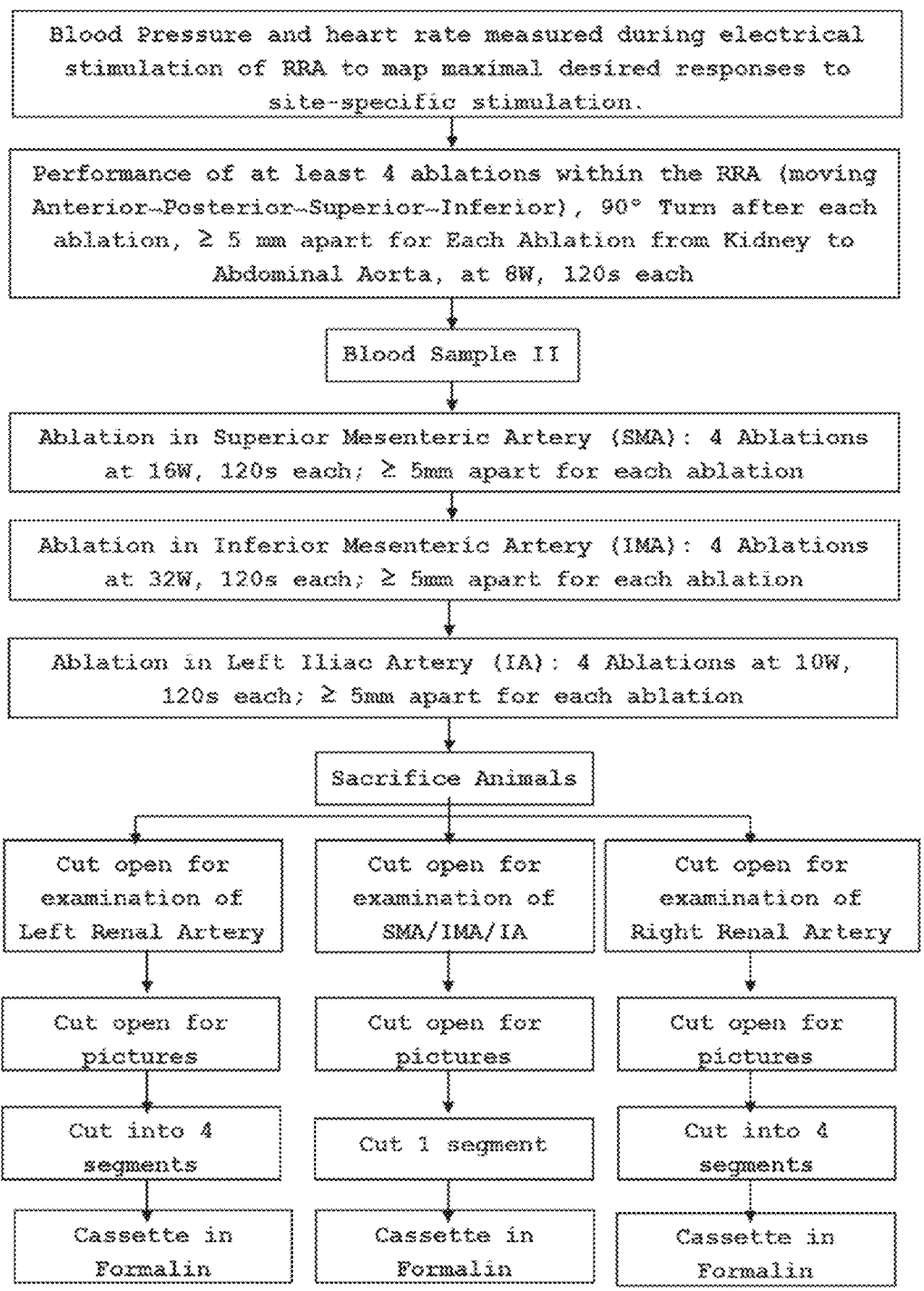
FIG. 3 shows the experimental setup for acute pig experiments used in nerve mapping experiments.

Three pigs (body weight from 50-52 kg) were anesthetized with intravenous injection of sodium pentobarbital at 15 mg/kg. The physiological parameters: systolic blood pressure, diastolic blood pressure, mean arterial pressure and heart rate were monitored. The experimental design and protocol are illustrated in FIG. 3.

The ablation catheter used in this set of experiments was the 7F, B-Type, spacing 2-5-2 mm, CELSIUS® RMT Diagnostic/Ablation Steerable Catheter (Biosense Webster, Diamond Bar, Calif. 91765, USA) and a Celsius radiofrequency generator (STOCKERT 70 RF Generator, Model Stockert GmbH EP-SHUTTLE ST-3205, STOCKERT GmbH, Freiburg, Germany).

Baselines for systolic, diastolic and mean arterial blood pressure and heart rate were measured before the delivery of electrical energy to different areas of the renal arterial wall. Mean arterial blood pressure and heart rate were then measured 5 seconds to 2 minutes after the delivery of energy to note for any effects. By recognizing that a significant change in blood pressure and heart rate to be associated with nerve stimulation, it was found that, although the segment of the arterial wall that is innervated varies in each animal, the method described herein has correctly located these areas in each of the animals giving a map of the innervated regions in the renal artery.

EXAMPLE 2

Relationship Between Physiological Parameters and the Nerves Innervating an Arterial Wall In order to demonstrate that energy delivered to different locations on an arterial wall may result in different effects on physiological parameters such as blood pressure and heart rate, and such characteristics can be capitalized on to identify the type of nerve innervating an arterial wall, electrical energy was delivered to the innervated areas on the renal arterial walls of the pig model according to several strategies. Detailed parameters on the electrical energy delivered to Pig #1, Pig #2 and Pig #3 are shown in Table 1, Table 2 and Table 3 respectively.

In Pig #1, four separate stimulations took place in the left renal artery and two separate stimulations were performed in the right renal artery. As preliminary approaches, on the abdominal side of the left renal artery, two separate doses of electrical energy were delivered: one to the anterior wall and one to the posterior wall of the artery. On the kidney side of the left renal artery, two separate doses of electrical energy were delivered: one to the anterior wall and one to the posterior wall of the artery. Different effects of these energies on blood pressure and heart rate were observed. In the right renal artery, one dose of electrical energy was delivered to the renal artery on the abdominal side and the kidney side, respectively. The same stimulation strategy was used for Pig #2 and Pig #3.

The electrical energy delivered to different locations in the renal artery caused different effects on the systolic blood pressure, diastolic blood pressure, mean blood pressure and heart rate in all of the pigs tested. For instance, in response to the electrical energy delivered to the left kidney, the maximal change in systolic blood pressure was respectively 19.5 mmHg and 29 mmHg in Pig #1 and Pig #3; the minimal change of systolic blood pressure was respectively 2 mmHg and 1 mmHg in Pig #1 and Pig #3. However, in Pig #2, changes in systolic blood pressure were consistent when the electrical energy was delivered to either the abdominal aorta side or the kidney side. Furthermore, the stimulation location which caused the maximal effect or minimal effect varied from animal to animal, indicating that the distribution of renal autonomic nerves is not consistent between animals. These phenomenons in systolic blood pressure, diastolic blood pressure, mean arterial blood pressure and heart rate during delivery of electrical energy to wall of the left renal artery were observed and further summarized in Table 4A, 4B, 4C and 4D, respectively. Similar phenomenon in systolic blood pressure, diastolic blood pressure, mean arterial blood pressure and heart rate during electrical stimulation in the right renal artery were also observed and further summarized in Table 5A, 5B, 5C and 5D, respectively.

Figure 4A:
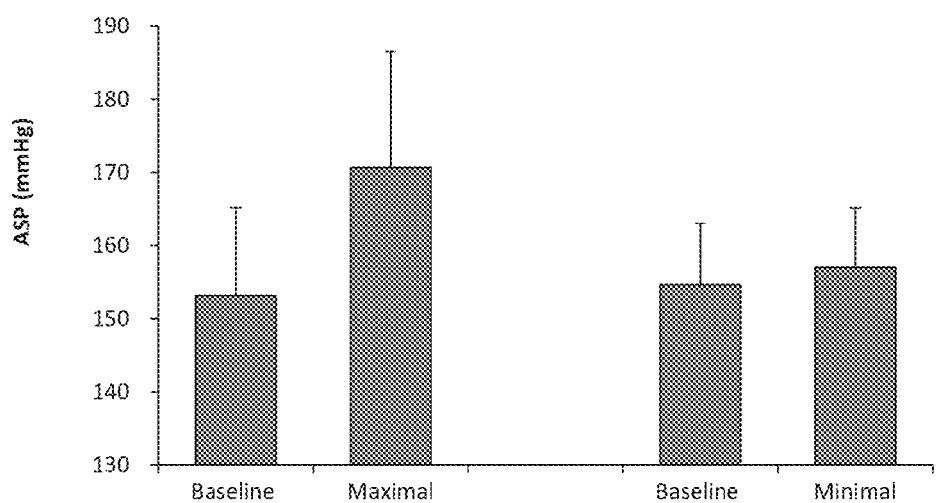
FIG. 4A shows Maximal and Minimal Effects of Left Renal Artery Stimulation on Arterial Systolic Pressure (ASP). Shown is arterial systolic pressure (ASP, as measured in mmHg) after an electrical stimulation in the left renal artery (LRA); baseline measures, as well maximal and minimal responses after the stimulation are shown.
Figure 4B:
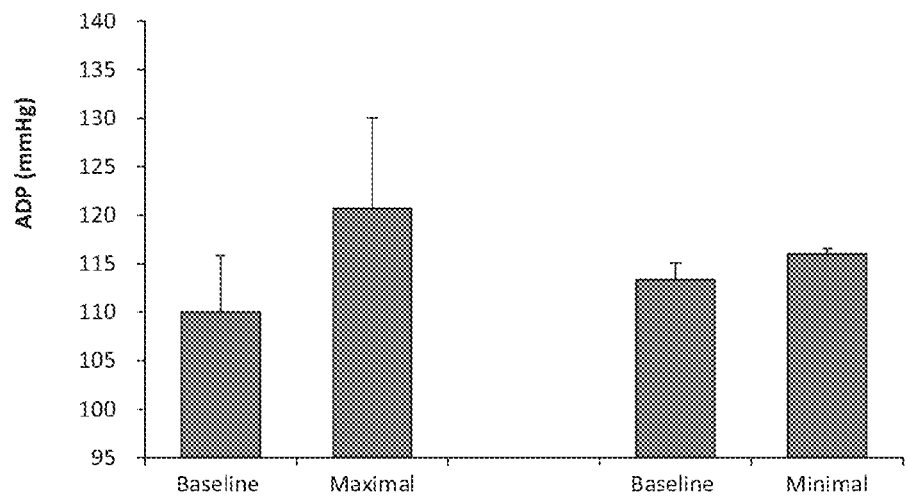
FIG. 4B shows Maximal and Minimal Effects of Left Renal Artery Stimulation on Arterial Diastolic Pressure (ADP). Shown is arterial diastolic pressure (ADP, as measured in mmHg) after an electrical stimulation in the left renal artery (LRA); baseline measures, as well as maximal and minimal responses after the stimulation are shown.
Figure 5A:
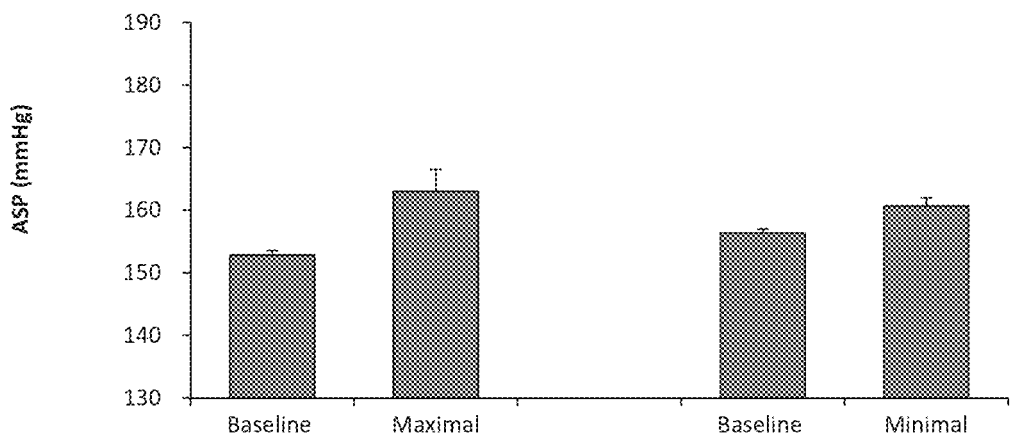
FIG. 5A shows Maximal and Minimal Effects of Right Renal Artery Stimulation on Arterial Systolic Pressure (ASP). Shown is arterial systolic pressure (ASP, as measured in mmHg) after stimulation in the right renal artery (RRA); baseline measures, as well maximal and minimal responses after an electrical stimulation are shown.
Figure 5B:
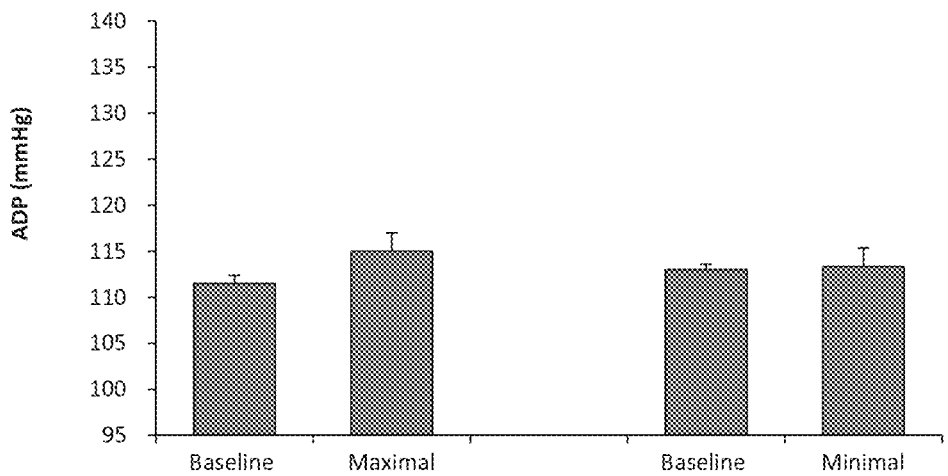
FIG. 5B shows Maximal and Minimal Effects of Right Renal Artery Stimulation on Arterial Diastolic Pressure (ADP). Shown is arterial diastolic pressure (ADP, as measured in mmHg) after an electrical stimulation in the right renal artery (RRA); baseline measures, as well as maximal and minimal responses after the stimulation are shown.
Figure 5C:
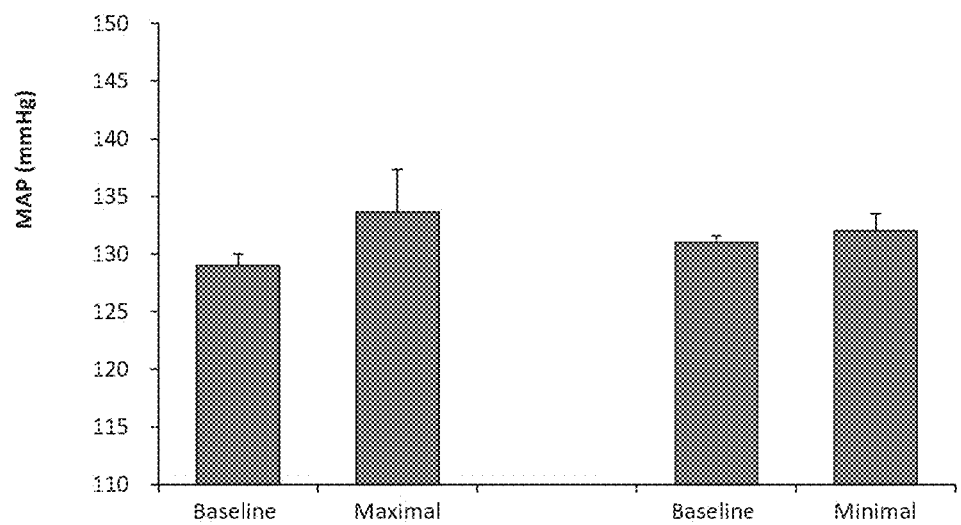
FIG. 5C shows mean arterial pressure (MAP, as measured in mmHg) after an electrical stimulation in the right renal artery (LRA); baseline measures, as well as maximal and minimal responses after the stimulation are shown.
Figure 5D:
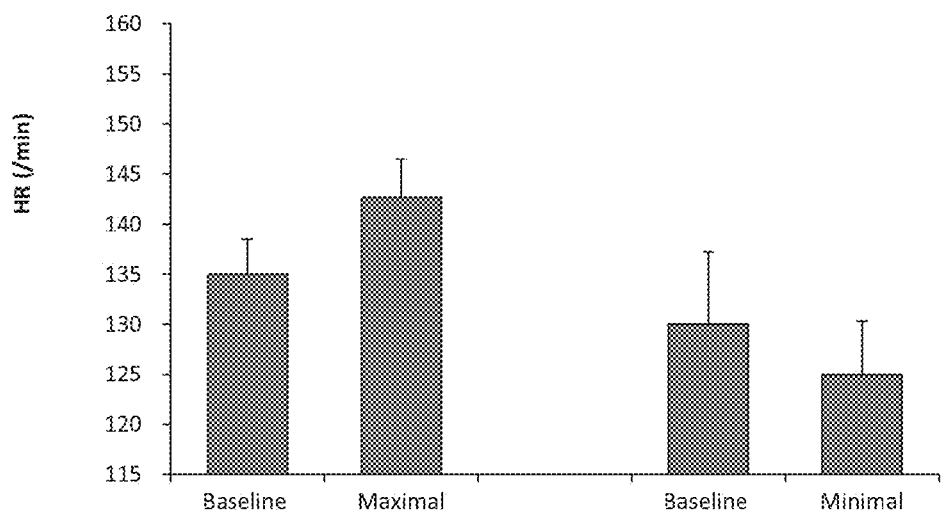
FIG. 5D shows Maximal and Minimal Effects of Right Renal Artery Stimulation on Heart Rate (HR). Shown are maximal and minimal changes in heart rate after right renal artery (RRA) electrical stimulation; baseline measures, as well as maximal and minimal heart rates after the stimulation are shown.

These data provide proof of concept for locating and identifying nerves innervating an arterial wall—specifically, that a substantial physiological response, in this case, the maximal increase or decrease in measured blood pressure, was induced by delivery of electrical energy via a catheter placed at a defined location where renal nerve branches are abundantly distributed. Averaged data (mean±SD) calculated from Tables 4A-D and Tables 5A-D are graphically represented in FIG. 4 and FIG. 5, inclusive of all sub-figures.

TABLE 1

Renal Nerve Stimulation for Mapping
Pig #1:

| Renal Artery | Stimulation Site | | Stimulation Parameters |
|---|---|---|---|
| Left | Kidney side | Anterior Wall | 15 V; 0.4 ms; 400 Ohm; 17 mA |
| | | Posterior Wall | 15 V; 0.4 ms; 400 Ohm; 28 mA |
| | Abdominal Aorta Side | Anterior Wall | 15 V; 0.2 ms; 400 Ohm; 28 mA |
| | | Posterior Wall | 15 V; 0.2 ms; 540 Ohm; 28 mA |
| Right | Kidney side | | 15 V; 0.2 ms; 600 Ohm; 25 mA |
| | Abdominal Aorta Side | | 15 V; 0.2 ms; 520 Ohm; 25 mA |

TABLE 2

Renal Nerve Stimulation for Mapping
Pig #2:

| Renal Artery | Stimulation Site | Stimulation Parameters |
|---|---|---|
| Left | Kidney side | 15 V; 0.2 ms; 580 Ohm; 26 mA |
| | Abdominal Aorta Side | 15 V; 0.2 ms; 480 Ohm; 28 mA |
| Right | Kidney side | 15 V; 0.2 ms; 520 Ohm; 28 mA |
| | Abdominal Aorta Side | 15 V; 0.2 ms; 500 Ohm; 28 mA |

TABLE 3

Renal Nerve Stimulation for Mapping
Pig #3:

| Renal Artery | Stimulation Site | Stimulation Parameters |
|---|---|---|
| Left | Kidney side | 15 V; 9.9 ms; 800 Ohm; 28 mA |
| | Abdominal Aorta Side | 15 V; 9.9 ms; 800 Ohm; 28 mA |
| Right | Kidney side | 15 V; 9.9 ms; 800 Ohm; 28 mA |
| | Abdominal Aorta Side | 15 V; 9.9 ms; 800 Ohm; 28 mA |

TABLE 4A

Changes in Systolic Blood Pressure (SBP) During
Electrical Stimulation in Left Renal Artery

| | Left Renal Stimulation | | | | | | | |
|---|---|---|---|---|---|---|---|---|
| SBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 131.5 | 151 | 19.5 | AO Side | 140 | 142 | 2 | Renal Side |
| Pig 2 | 155 | 159 | 4 | Renal Side | 155 | 159 | 4 | AO Side |
| Pig 3 | 173 | 202 | 29 | Renal Side | 169 | 170 | 1 | AO Side |
| Average | 153.2 | 170.7 | 17.5 | | 154.7 | 157.0 | 2.3 | |
| SD | 20.8 | 27.4 | 12.6 | | 14.5 | 14.1 | 1.5 | |

TABLE 4B

Changes in Diastolic Blood Pressure (DBP) During
Electrical Stimulation in Left Renal Artery

| | Left Renal Stimulation | | | | | | | |
|---|---|---|---|---|---|---|---|---|
| DBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 99 | 108 | 9 | AO Side | 116 | 117 | 1 | Renal Side |
| Pig 2 | 112 | 115 | 3 | Renal Side | 114 | 116 | 2 | AO Side |
| Pig 3 | 119 | 139 | 20 | Renal Side | 110 | 115 | 5 | AO Side |
| Average | 110.0 | 120.7 | 10.7 | | 113.3 | 116.0 | 2.7 | |
| SD | 10.1 | 16.3 | 8.6 | | 3.1 | 1.0 | 2.1 | |

TABLE 4C

Changes in Mean Arterial Pressure (MAP) During
Electrical Stimulation in Left Renal Artery

| | Left Renal Stimulation | | | | | | | |
|---|---|---|---|---|---|---|---|---|
| MAP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 112.5 | 125 | 12.5 | AO Side | 123 | 128 | 5 | Renal Side |
| Pig 2 | 130 | 133 | 3 | Renal Side | 131 | 132 | 1 | AO Side |
| Pig 3 | 141 | 158 | 17 | Renal Side | 136 | 138 | 2 | AO Side |
| Average | 127.8 | 138.7 | 10.8 | | 130.0 | 132.7 | 2.7 | |
| SD | 14.4 | 17.2 | 7.1 | | 6.6 | 5.0 | 2.1 | |

TABLE 4D

Changes in Heart Rate (HR) During Electrical Stimulation in Left Renal Artery

| HR | Left Renal Stimulation | | | | | | |
|---|---|---|---|---|---|---|---|
| | Maximal Responses (beats/min) | | | | Minimal Responses (beats/min) | | |
| Animal No. | Baseline | Maximal | Δ | Stimulation Location | Baseline | Minimal | Δ | Stimulation Location |
| Pig 1 | 150 | 151 | 1 | Renal Side | 140 | 130 | −10 | Renal Side |
| Pig 2 | 126 | 132 | 6 | AO Side | 132 | 120 | −12 | Renal Side |
| Pig 3 | 138 | 142 | 4 | Renal Side | 159 | 150 | −9 | AO Side |
| Average | 138.0 | 141.7 | 3.7 | | 143.7 | 133.3 | −10.3 | |
| SD | 12.0 | 9.5 | 2.5 | | 13.9 | 15.3 | 1.5 | |

TABLE 5A

Changes in Systolic Blood Pressure (SBP) During Electrical Stimulation in Right Renal Artery

| SBP | Right Renal Stimulation | | | | | | | |
|---|---|---|---|---|---|---|---|---|
| | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 151.5 | 156 | 4.5 | Renal Side | 155 | 158 | 3 | AO Side |
| Pig 2 | 153 | 166 | 13 | Renal Side | 157 | 162 | 5 | AO Side |
| Pig 3 | 154 | 167 | 13 | Renal Side | 157 | 162 | 5 | AO Side |
| Average | 152.8 | 163.0 | 10.2 | | 156.3 | 160.7 | 4.3 | |
| SD | 1.3 | 6.1 | 4.9 | | 1.2 | 2.3 | 1.2 | |

TABLE 5B

Changes in Diastolic Blood Pressure (DBP) During Electrical Stimulation in Right Renal Artery

| DPB | Right Renal Stimulation | | | | | | | |
|---|---|---|---|---|---|---|---|---|
| | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 111.5 | 113 | 1.5 | Renal Side | 113 | 113 | 0 | AO Side |
| Pig 2 | 113 | 119 | 6 | Renal Side | 114 | 117 | 3 | AO Side |
| Pig 3 | 110 | 113 | 3 | Renal Side | 112 | 110 | −2 | AO Side |
| Average | 111.5 | 115.0 | 3.5 | | 113.0 | 113.3 | 0.3 | |
| SD | 1.5 | 3.5 | 2.3 | | 1.0 | 3.5 | 2.5 | |

TABLE 5C

Changes in Mean Arterial Pressure (MAP) During Electrical Stimulation in Right Renal Artery

| MAP | Right Renal Stimulation | | | | | | | |
|---|---|---|---|---|---|---|---|---|
| | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 130 | 130 | 0 | AO Side | 131 | 130 | −1 | Renal Side |
| Pig 2 | 130 | 141 | 11 | Renal Side | 132 | 135 | 1 | AO Side |
| Pig 3 | 127 | 130 | 3 | Renal Side | 130 | 131 | 1 | AO Side |
| Average | 129.0 | 133.7 | 4.7 | | 131.0 | 132.0 | 1.0 | |
| SD | 1.7 | 6.4 | 5.7 | | 1.0 | 2.6 | 2.0 | |

TABLE 5D

Changes in Heart Rate (HR) During Electrical Stimulation in Right Renal Artery

| HR | Right Renal Stimulation | | | | | | | |
|---|---|---|---|---|---|---|---|---|
| | Maximal Responses (beats/min) | | | | Minimal Responses (beats/min) | | | |
| Animal No. | Baseline | Maximal | Δ | Stimulation Location | Baseline | Minimal | Δ | Stimulation Location |
| Pig 1 | 141 | 146 | 5 | AO Side | 144 | 135 | −9 | Renal Side |
| Pig 2 | 135 | 147 | 12 | Renal Side | 120 | 117 | −3 | AO Side |
| Pig 3 | 129 | 135 | 6 | Renal Side | 126 | 123 | −3 | AO Side |
| Average | 135.0 | 142.7 | 7.7 | | 130.0 | 125.0 | −5.0 | |
| SD | 6.0 | 6.7 | 3.8 | | 12.5 | 9.2 | 3.5 | |

TABLE 6

Possible effects of stimulating renal nerves

| Publication | Animal Model | Change of blood pressure when renal nerve stimulated | Change of heart rate when renal nerve stimulated |
|---|---|---|---|
| Ueda H, Uchida Y and Kamisaka K, "Mechanism of the Reflex Depressor Effect by Kidney in Dog", | Dog | ↓ | N/A |
| Beacham W S and Kunze DL., "Renal Receptors Evoking a Spinal Vasometer Reflex", J. Physiol., 1969, 201 (1): 73-85 | Cat | ↓ | N/A |
| Aars H and Akre S "Reflex Changes in Sympathetic Activity and Arterial Blood Pressure Evoked by | Rabbit | ↓ | N/A |

TABLE 6-continued

Possible effects of stimulating renal nerves

| Publication | Animal Model | Change of blood pressure when renal nerve stimulated | Change of heart rate when renal nerve stimulated |
|---|---|---|---|
| *Afferent Stimulation of the Renal Nerve*", Acta Physiol. Scand., 1970, 78 (2): 184-188 | | | |
| Ma G and Ho SY, "*Hemodynamic Effects of Renal Interoreceptor and Afferent Nerve Stimulation in Rabbit*", Acta Physiol. Sinica, 1990, 42 (3): 262-268 | Rabbit | ↓ | ↓ |
| Lu M, Wei S G and Chai XS, "*Effect of Electrical Stimulation of Afferent Renal Nerve on Arterial Blood Pressure, Heart Rate and Vasopressin in Rabbits*", Acta Physiol. Sinica, 1995, 47 (5): 471-477 | Rabbit | ↓ | ↓ |

Figure 6:
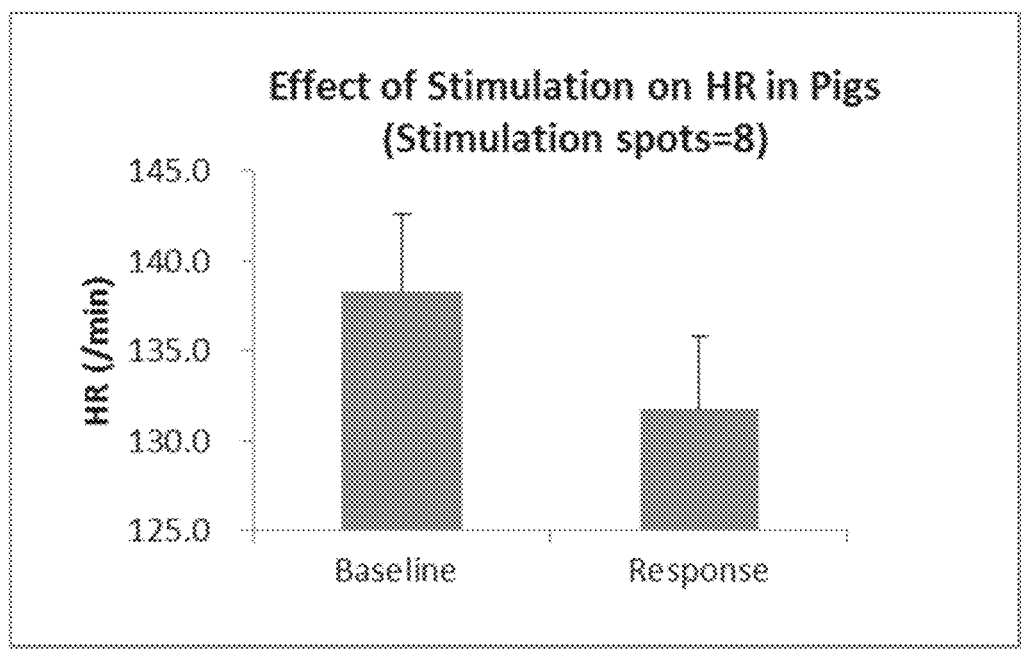
FIG. 6 shows the decreases in heart rate once intra-renal artery stimulations were applied to certain locations of renal artery.
Figure 7A:
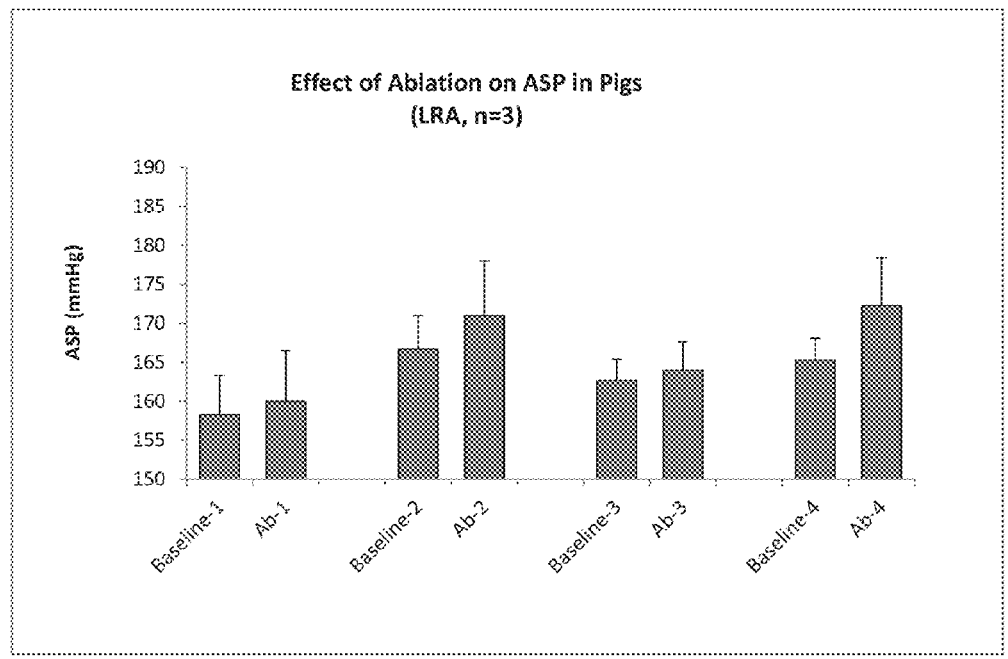
FIG. 7A shows Changes in Arterial Systolic Pressure (ASP) during Four Separated Renal Ablation in Left Renal Artery. Shown are the changes in arterial systolic pressure (ASP, as measured in mmHg) during four separate renal ablations in the left renal artery (LRA).
Figure 7B:
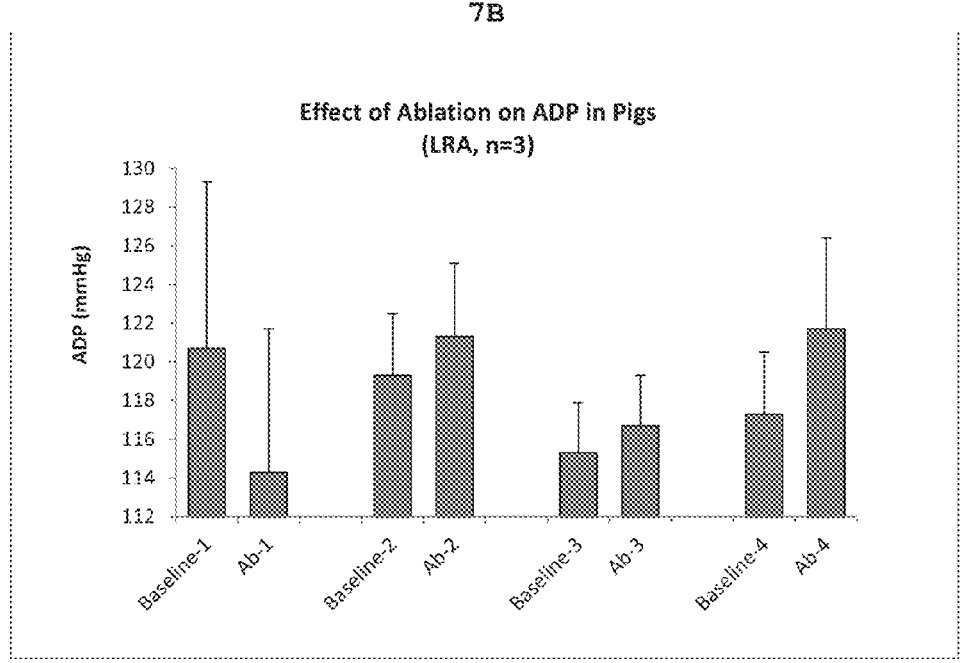
FIG. 7B shows Changes in Arterial Diastolic Pressure (ADP) during Four Separated Renal Ablation in Left Renal Artery. Shown are changes in arterial diastolic pressure (ADP, as measured in mmHg) during four separate renal ablations in the left renal artery (LRA).
Figure 7C:
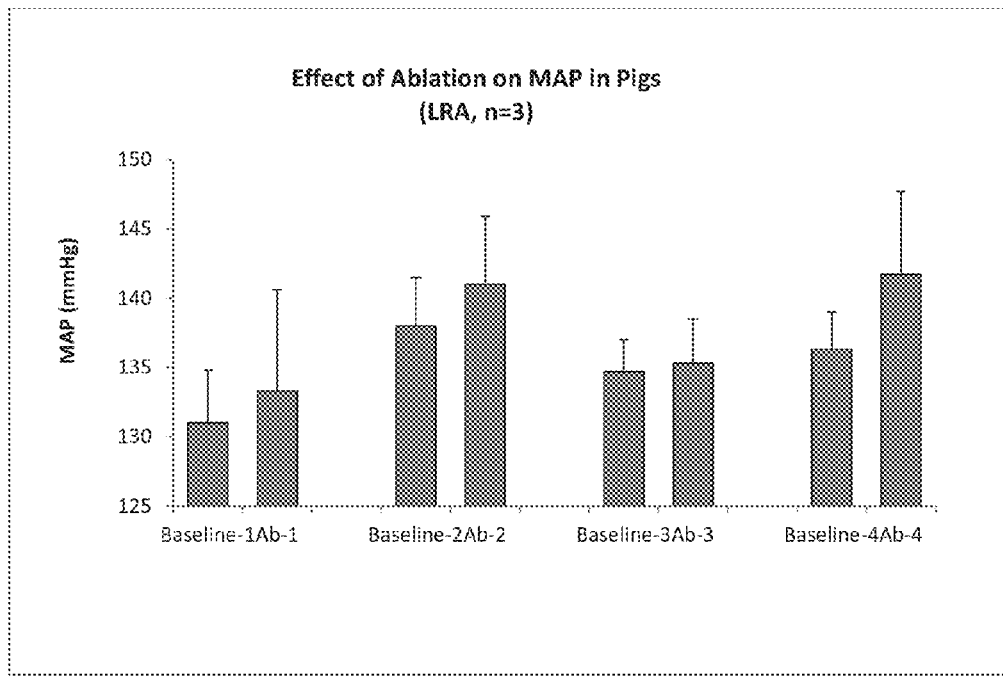
FIG. 7C shows Changes in Mean Arterial Pressure (MAP) during Four Separated Renal Ablation in Left Renal Artery. Shown are changes in mean arterial pressure (MAP, as measured in mmHg) during four separate renal ablations in the left renal artery (LRA).
Figure 7D:
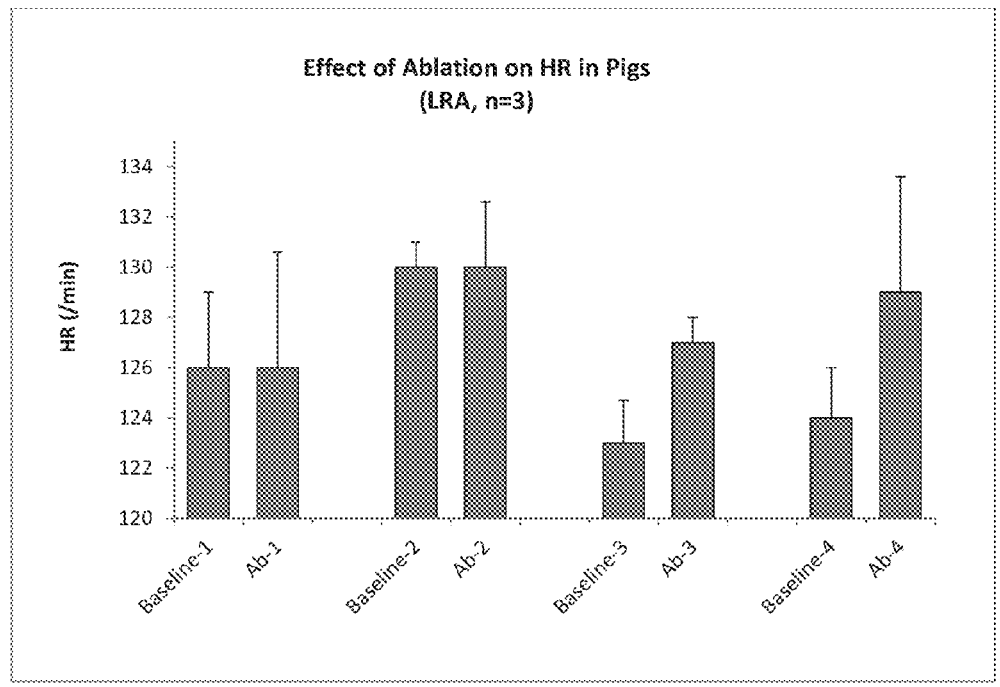
FIG. 7D shows Changes in Heart Rate (HR) during Four Separated Renal Ablation in Left Renal Artery. Shown are changes in heart rate during four separate renal ablations in the left renal artery (LRA).
Figure 8A:
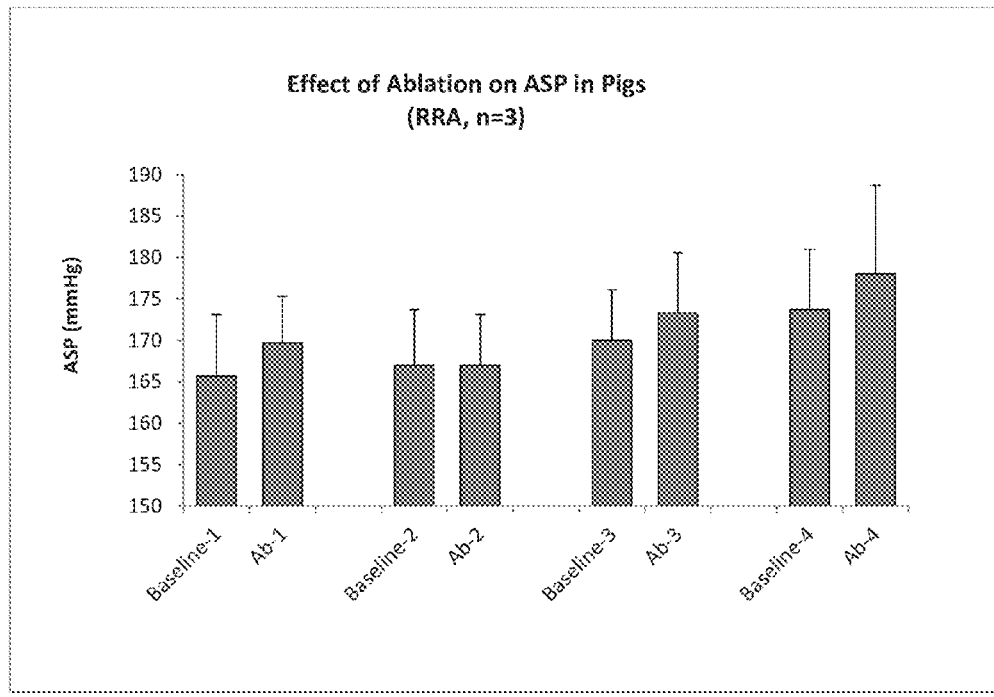
FIG. 8A shows Changes in Arterial Systolic Pressure (ASP) during Four Separated Renal Ablation in Right Renal Artery. Shown are changes in arterial systolic pressure (ASP, as measured in mmHg) during four separate renal ablations in the right renal artery (RRA).
Figure 8B:
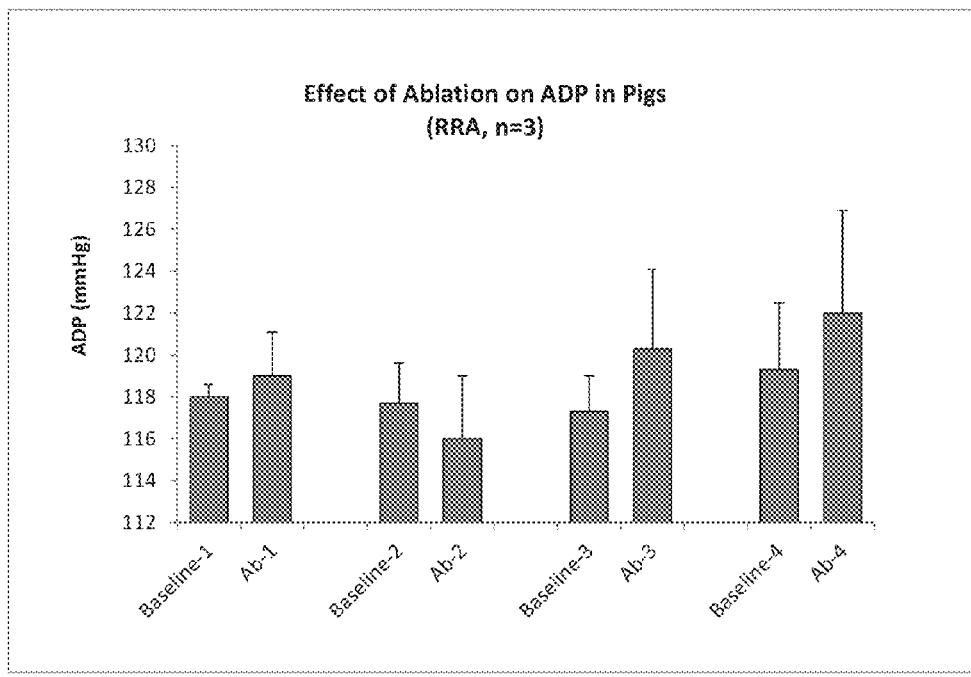
FIG. 8B shows Changes in Arterial Diastolic Pressure (ADP) during Four Separated Renal Ablation in Right Renal Artery. Shown are changes in arterial diastolic pressure (ADP, as measured in mmHg) during four separate renal ablations in the right renal artery (RRA).
Figure 8C:
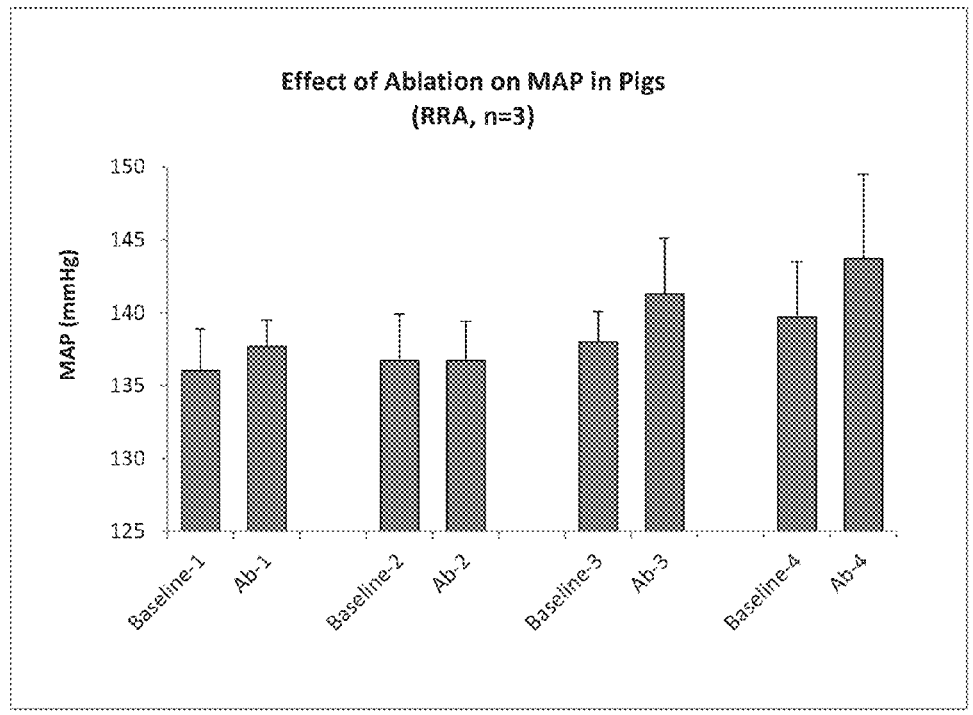
FIG. 8C Changes in Mean Arterial Pressure (MAP) during Four Separated Renal Ablation in Right Renal Artery. Shown are changes in mean arterial pressure (MAP, as measured in mmHg) during four separate renal ablations in the right renal artery (RRA).
Figure 8D:
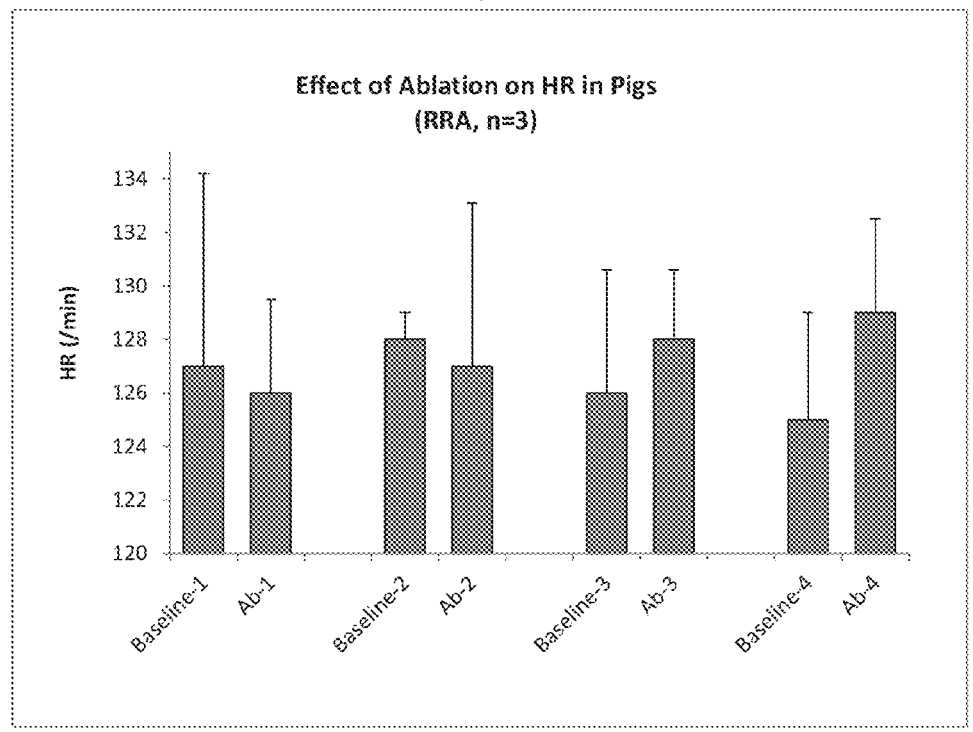
FIG. 8D shows Changes in Heart Rate (HR) during Four Separated Renal Ablation in Right Renal Artery. Shown are changes in heart rate during four separate renal ablations in the right renal artery (RRA).

Among all the stimulation experiments performed in pigs according to the previously described protocol, certain locations in the renal arterial wall led to significant decreases in heart rate without causing changes in the blood pressure or the change in blood pressure is minimal in comparison to the decrease in heart rate (FIG. 6). Slight decreases in blood pressure, especially, diastolic blood pressure were often recorded. Out of the 56 data points inclusive of all 4 physiological parameters evaluated in the experiments, there were at least 1 data point from each physiological parameter that responded with the dose of energy by a drop or no/insignificant change in value; this accounted for over 23% of the data points in this experiment. These distinctive physiological changes in response to the stimulations appear to indicate that nerves innervating these locations are of parasympathetic nature and are different from those sympathetic nerves innervating the locations that results in increases in blood pressure and heart rate upon stimulation. Table 6 summarized the effect of delivering a suitable dose of energy to the afferent renal nerve in different studies involving animal models of dogs, cats and rabbits. In conjunction with this invention, the studies in Table 6 had demonstrated that it is not uncommon to induce effects akin to parasympathetic activity when a suitable dose of energy is delivered to the nerves innervating the kidney. In other words, there is an indication that, in the neural circuitry of the renal artery, there exist nerves that can induce parasympathetic activity rather than sympathetic activity and therefore should not be ablated when treating blood pressure related diseases.

EXAMPLE 3

Ensuring Energy is Directed to a Target Nerve During Ablation

Subsequent to the studies for locating and identifying nerves in an arterial wall, energies at dosage suitable for ablations were also delivered to the innervated spots in the renal arterial wall of the same pigs. Four ablations were each delivered to the left and to the right renal arteries starting from the kidney side and moving to the abdominal aorta side in the order of movement from the anterior, to the posterior, to the superior and then to the inferior wall; each ablation was ≤5 mm apart from the location of the previous ablation and the electrode head (catheter tip) of the ablation catheter was turned 90 degrees after each ablation. Based on the literature (Krum 2009, 2010), low energy level (5-8 watts) should be used for renal ablation; therefore, 5 watts and 8 watts were used for renal ablation. For left renal artery ablation, the energy level applied was 5 watts and the time length of ablation was 120 seconds; for the right renal artery, the ablation energy level applied was 8 watts and the time length was 120 seconds. The temperature at the ablation site was measured to be from 40° C. to 50° C. The physiological parameters: systolic blood pressure, diastolic blood pressure, mean arterial pressure and heart rate were examined during ablations. The data clearly showed that ablation at different locations within the renal artery resulted in differing changes in blood pressure and heart rate, further demonstrating that changes in physiological parameters such as blood pressure and heart rate can be used as indicators for an accurate delivery of ablation energy to a targeted nerve and provided further evidence that distribution of the nerves in the arterial wall varied case by case.

Changes in systolic blood pressure, diastolic blood pressure, mean arterial pressure and heart rate during four separate renal ablations in the renal arteries of the left kidney were summarized in FIGS. 7A, 7B, 7C and 7D, respectively. Changes in arterial systolic and diastolic pressure, mean arterial pressure and heart rate during four separate renal ablations in the renal arteries of the right kidney were summarized in FIGS. 8A, 8B, 8C and 8D, respectively.

REFERENCES

1. Aars, H. and Akre, S., (1970), Reflex Changes in Sympathetic Activity and Arterial Blood Pressure Evoked by Afferent Stimulation of the Renal Nerve, Acta Physiol. Scand., 78 (2): 184-188.
2. Beacham, W. S. and Kunze, D. L., (1969), Renal Receptors Evoking a Spinal Vasometer Reflex, J. Physiol., 201(1): 73-85.
3. DiBona, G. F. (2003), Neural control of the kidney: past, present and future, Hypertension, 41: 621-624.
4. Esler, M., Schlaich, M., Sobotka, P. et al., (2009) Catheter-based renal denervation reduces total body and renal noradrenaline spillover and blood pressure in resistant hypertension, Journal of Hypertension, 27(suppl 4):s167.
5. Esler, M. et al., (Dec. 4, 2010), Renal sympathetic denervation in patients with treatment-resistant hypertension (The Symplicity HTN-2 Trial): a randomized controlled study, The Lancet, 376: 1903-1909.

6. Krum, H., Schlaich, M., Whitbourn, R., Sobotka, P. A., Sadowski, J., Krzysztof, Bartus, K., Kapelak, B., Walton, A., Sievert, H., Thambar, S., Abraham, W. T., and Esler, M., (April 2009), Catheter-based renal sympathetic denervation for resistant hypertension: a multicentre safety and proof-of-principle cohort study, The Lancet, 373(9671): 1275-1281.
7. Lu, M., Wei, S. G. and Chai, X. S., (1995), Effect of Electrical Stimulation of Afferent Renal Nerve on Arterial Blood Pressure, Heart Rate and Vasopressin in Rabbits, Acta Physiol. Sinica, 47 (5): 471-477.
8. Ma, G. and Ho, S. Y., (1990), Hemodynamic Effects of Renal Interoreceptor and Afferent Nerve Stimulation in Rabbit, Acta Physiol. Sinica, 42 (3): 262-268.
9. Medical devices: pg 1-2, Feb. 22, 2012.
10. Smithwick, R. H., and Thompson, J. E., (Aug. 15, 1953), Splanchnicectomy for essential hypertension; results in 1,266 cases. J Am Med Association, 152(16):1501-1504.
11. Ueda, H., Uchida, Y., and Kamisaka, K., (1967), Mechanism of the Reflex Depressor Effect by Kidney in Dog, Jpn. Heart J., 8 (6): 597-606.
12. Wang, J., Mapping sympathetic nerve distribution for renal ablation and catheters for the same, US patent application no. 2011/0306851 A1, filed Aug. 26, 2011.

What is claimed is:

1. A method of mapping parasympathetic or sympathetic renal nerve for treatment of disease caused by systemic renal nerve hyperactivity, comprising the steps of:
   a) introducing a catheter into the lumen of a renal artery such that the tip of said catheter contacts a site on the inner renal artery wall;
   b) measuring one or more physiological parameters to obtain baseline measurements before introducing electrical current to the site, said one or more physiological parameters are selected from the group consisting of systolic blood pressure, diastolic blood pressure, mean arterial pressure, and heart rate;
   c) applying electrical stimulation by introducing electrical current to the site via the catheter, wherein said electrical current is controlled to be sufficient to elicit changes in said one or more physiological parameters when there is an underlying nerve at the site; and
   d) measuring said one or more physiological parameters at a specific time interval after each electrical stimulation, wherein an increase of said one or more physiological parameters over the baseline measurements after said electrical stimulation would indicate that a sympathetic renal nerve has been mapped at said site; a decrease of said one or more physiological parameters over the baseline measurements after said electrical stimulation would indicate that a parasympathetic renal nerve has been mapped at said site.

2. The method of claim 1, wherein said catheter is an ablative catheter currently in use to treat cardiac arrhythmias.

3. The method of claim 1, wherein said catheter is an ablative catheter designed specifically for mapping renal nerves for ablative procedures.

4. The method of claim 1, further comprises the step of applying radiofrequency energy through the catheter to the site identified in step (d) for ablation of the underlying nerve to treat disease caused by systemic renal nerve hyperactivity.

5. The method of claim 4, further comprises repeating the steps (b) to (d) on the ablated site, wherein a lack of change in said one or more physiological parameters confirms nerve ablation.

6. A system when used for mapping parasympathetic or sympathetic renal nerve, comprising:
   (i) a catheter configured to deliver electrical current to one or more locations on the inner renal artery wall sufficient to stimulate a nerve innervating said renal artery;
   (ii) one or more measuring devices for measuring one or more physiological parameters associated with the innervation of said renal artery, wherein said one or more physiological parameters are selected from the group consisting of systolic blood pressure, diastolic blood pressure, mean arterial blood pressure, and heart rate;
   (iii) a computing device configured to couple to the one or more measuring devices, wherein said computing device computes a baseline for said one or more physiological parameters prior to delivery of said electrical current and computes any increase or decrease in the physiological parameters against said baseline after delivery of said electrical current; and
   (iv) a display device for displaying the location or identity of a nerve innervating said inner renal artery wall, wherein said display device will display signal for sympathetic nerve when said one or more physiological parameters increase relative to said baseline, and wherein said display device will display signal for parasympathetic nerve when said one or more physiological parameters decrease relative to said baseline.

7. The system of claim 6, wherein said measuring devices are placed inside the renal artery, femoral artery or outside the body.

8. The system of claim 6, wherein said catheter could also deliver ablative energy selected from the group consisting of radiofrequency, mechanical, ultrasonic, radiation, optical and thermal energies.

9. The system of claim 6, wherein said computing device comprises one or more microcontrollers or computers.

10. The system of claim 6, wherein the location or identity of the parasympathetic or sympathetic nerve is displayed as numbers, texts, symbols, colors, sound, waveforms, or a combination thereof.

11. The system of claim 6, wherein said catheter is an ablative catheter currently in use to treat cardiac arrhythmias.

12. The system of claim 6, wherein said catheter is an ablative catheter designed specifically for mapping renal nerves for ablative procedures.

13. A method of using the system of claim 6 for mapping parasympathetic or sympathetic renal nerve, comprising the steps of:
   a) introducing a catheter into the lumen of a renal artery such that the tip of said catheter contacts a site on the inner renal artery wall;
   b) measuring one or more physiological parameters to obtain baseline measurements before introducing electrical current to the site, said one or more physiological parameters are selected from the group consisting of systolic blood pressure, diastolic blood pressure, mean arterial pressure, and heart rate;
   c) applying electrical stimulation by introducing electrical current to the site via the catheter, wherein said electrical current is controlled to be sufficient to elicit changes in said one or more physiological parameters when there is an underlying nerve at the site; and
   d) measuring said one or more physiological parameters at a specific time interval after each electrical stimulation, wherein an increase of said one or more physiological parameters over the baseline measurements after said electrical stimulation would indicate that a sympathetic renal nerve has been mapped at said site; a decrease of said one or more physiological parameters over the baseline measurements after said electrical stimulation would indicate that a parasympathetic renal nerve has been mapped at said site.

14. The method of claim 13, wherein said catheter is an ablative catheter currently in use to treat cardiac arrhythmias.

15. The method of claim 13, wherein said catheter is an ablative catheter designed specifically for mapping renal nerves for ablative procedures.

16. The method of claim 13, further comprises the step of applying radiofrequency energy through the catheter to the site identified in step (d) for ablation of the underlying nerve to treat disease caused by systemic renal nerve hyperactivity.

17. The method of claim 16, further comprises repeating the steps (b) to (d) on the ablated site, wherein a lack of change in said one or more physiological parameters confirms nerve ablation.

\* \* \* \* \*